(12) United States Patent
Gordon et al.

(10) Patent No.: US 9,721,217 B2
(45) Date of Patent: Aug. 1, 2017

(54) METHODS AND SYSTEMS FOR BUSINESS DEVELOPMENT AND LICENSING AND COMPETITIVE INTELLIGENCE

(71) Applicants: Mark Gordon, Carmel, IN (US); Tim Miller, Chislehurst (GB); Mans A Olof-Ors, Baar (CH); Hassan Malik, Monmouth Junction, NJ (US); Andrej Bugrim, St. Joseph, MI (US); Colin Williams, Aylesbury (GB)

(72) Inventors: Mark Gordon, Carmel, IN (US); Tim Miller, Chislehurst (GB); Mans A Olof-Ors, Baar (CH); Hassan Malik, Monmouth Junction, NJ (US); Andrej Bugrim, St. Joseph, MI (US); Colin Williams, Aylesbury (GB)

(73) Assignee: Camelot UK Bidco Limited, London (GB)

( * ) Notice: Subject to any disclaimer, the term of this patent is extended or adjusted under 35 U.S.C. 154(b) by 187 days.

(21) Appl. No.: 13/914,393

(22) Filed: Jun. 10, 2013

(65) Prior Publication Data
US 2014/0164008 A1    Jun. 12, 2014

Related U.S. Application Data

(63) Continuation of application No. 13/709,047, filed on Dec. 9, 2012, now abandoned.

(51) Int. Cl.
*G06Q 50/22* (2012.01)
*G06Q 50/24* (2012.01)
(Continued)

(52) U.S. Cl.
CPC .......... *G06Q 10/06* (2013.01); *G06Q 30/018* (2013.01); *G06Q 50/184* (2013.01); *G06Q 50/22* (2013.01)

(58) Field of Classification Search
CPC ...... G06Q 10/06; G06Q 20/145; G06Q 30/06; G06Q 50/18; G06Q 50/22; G06Q 50/184;
(Continued)

(56) References Cited

U.S. PATENT DOCUMENTS

| 3,108,635 A | 8/2000 | Herren et al. |
| 7,778,851 B2 * | 8/2010 | Schoenberg et al. ............. 705/3 |

(Continued)

OTHER PUBLICATIONS

Fernandez, J., Stein, R., and Lo, A. Commercializing Biomedical Research Through Securitization Techniques. [online] (Sep. 7, 2012) [retrieved on Feb. 23] retrieved from internet: <URL: http://dspace.mit.edu/openaccess-disseminate/1721.1/78287>.

*Primary Examiner* — Maroun Kanaan
(74) *Attorney, Agent, or Firm* — Duncan Galloway Egan Greenwald, PLLC; Kevin T. Duncan

(57) ABSTRACT

Systems and method for making intelligent business development and licensing decisions are disclosed. The present invention generally relates to an analytical tool that combines multiple data and content sets based on user selected factors and presents the data in the form of manipulatable visualizations to facilitate decision making to address a specific business problem. More specifically, this invention relates to providing a single portal for access to a decision support system that enables the visualization of data from multiple content and data sets to facilitate decision making related to opportunities analysis, asset acquisition, and intellectual property licensing.

28 Claims, 16 Drawing Sheets

(51) Int. Cl.
*G06Q 10/06* (2012.01)
*G06Q 30/00* (2012.01)
*G06Q 50/18* (2012.01)

(58) Field of Classification Search
CPC .... G06Q 50/24; G06Q 10/00; G06Q 10/0635; G06Q 10/06375; G06Q 10/1053; G06F 19/3443; G06F 19/345; G06F 19/3418
See application file for complete search history.

(56) References Cited

U.S. PATENT DOCUMENTS

| | | |
|---|---|---|
| 2003/0009355 A1 | 1/2003 | Gupta |
| 2005/0108047 A1* | 5/2005 | David ................. G06Q 50/22 705/2 |
| 2008/0086337 A1 | 4/2008 | Soon-Shiong |
| 2012/0179002 A1* | 7/2012 | Brunetti ............... G06F 19/345 600/300 |
| 2012/0185266 A1 | 7/2012 | Trifunov |
| 2012/0215554 A1 | 8/2012 | Yurkovich |

\* cited by examiner

METHODS AND SYSTEMS FOR BUSINESS DEVELOPMENT AND LICENSING AND COMPETITIVE INTELLIGENCE

CROSS REFERENCE TO RELATED APPLICATION

The present application claims benefit of priority to and is a continuation of U.S. patent application Ser. No. 13/709,047, filed Dec. 12, 2012, and entitled METHODS AND SYSTEMS FOR BUSINESS DEVELOPMENT AND LICENSING AND COMPETITIVE INTELLIGENCE (Gordon et. al.), which is hereby incorporated by reference herein in its entirety.

FIELD OF THE INVENTION

This invention generally relates to an analytical tool that combines multiple data and content sets based on user selected factors and presents the data in the form of manipulatable visualizations to facilitate decision making to address a specific business problem. More specifically, this invention relates to providing a single portal for access to a decision support system that enables the visualization of data from multiple content and data sets to facilitate decision making related to opportunities analysis, asset or product acquisition, asset or product development, and intellectual property licensing.

BACKGROUND OF THE INVENTION

The areas of pharmaceutical and biopharmaceutical research and development with respect to business development and licensing is very complex, and making any decisions as to what drugs or disease targets to research and/or develop, or what companies to partner with or enter into licensing or research agreements with requires sifting through and organizing large amounts of data, including unstructured data and often unrelated data. The problem faced by corporations engaged in pharmaceutical research and development is the daunting task of processing and making use of the immense and growing data sources available to make intelligent business decisions. Pharmaceutical corporations are also faced with the problem of identifying development, partnership, and acquisition opportunities before their competitors act on such opportunities. This process requires constant mining of scientific and financial information and assessment of this information against internal knowledge. There is currently no single place for this information to be searched, analyzed and processed.

A number of data products and services provide different sources of information that can be used in making business development and licensing decisions for a pharmaceutical company, however, these sources are disconnected and there is, at present, no easy way for a company to effectively utilize the disparate data sources in making effective business decisions. Furthermore, even if a company does sort through these different data sources, there does not exist an effective way to visually represent the collected data in a way that will aid in business development and licensing decisions.

Several companies and organizations exist that provide information (some of which may be publicly available or by subscription) that could be used by a pharmaceutical company in making business development and licensing decisions. Such entities and resources include many products, examples of which are Informa's Citeline (e.g., Pharma Projects, Medtrack, and Trial Trove), Adis, GlobalData, EvaluatePharma, PharmaVentures, Datamonitor, Venture Source, Deloitte Recap, and research journals such as PubMed and Medline. These and other resources are available to pharmaceutical companies wishing to research information to be used in making product development, acquisition, and licensing decisions. These data resource companies and services gather information from similar data sources and each provide their own features for searching and utilizing the data. However, none of these services provides a single source for searching both scientific and financial resources and for presenting the collected data in a manner that will enable a user to make effective business decisions.

In addition to information assets that pharmaceutical companies can utilize, there are software tools, such as Relay and Inova, and consulting firms that help companies identify and prioritize opportunities. Also available are "big data" solutions that mine unstructured data and present it in visual analytics tools. However, none of these solutions meets the industry need of a visual, analytical tool that uses intelligence to assist in decision making.

What is needed is a visual tool that uses a combination of scientific and financial intelligence, alongside internal corporate intelligence, to find whitespace or opportunities in the landscape of product development, potential acquisition, and partnership deals. Also, a system is needed that can process such information to identify and display patterns and trends that can be used in making effective business decisions.

SUMMARY OF THE INVENTION

To address the shortcomings of existing systems and to satisfy the present and long felt need of the marketplace, the present invention provides users with decision support tools to aid in identifying product development, acquisition, and licensing opportunities in the biopharmaceutical and pharmaceutical areas. For example, the present invention provides for the selection of a set of customizable factors to be weighted in accordance with the user's preference that are used to identify a set of assets associated with a disease, disease target, company/organization, or drug. The information collected and presented by the invention will help users make mergers and acquisitions decisions, build vs. buy decisions, licensing and other decisions related to business development, and conduct competitive analyses. The present invention may also be used to perform valuations on pharmaceuticals, pharmaceutical companies, and related intellectual property and to generate representations, expressions and/or visualizations of medical issues, drugs, companies, industries and valuations. As used herein the term medical issue should be interpreted broadly to include: a drug, a treatment, a disease, a biologic, an area of focus in pharmaceutical or biopharmaceutical research and development.

The present invention allows a user to select a medical issue, e.g., a drug or biological disease target, that the user is interested in researching or evaluating for buy or build decisions. The invention uses a combination of competitive intelligence on the disease target, close or similar disease targets, drugs in development against those disease targets, research being published about them, patents being filed on them, the companies developing the drugs, the private equity investments in those companies, the merger and acquisition activity involving those companies, and the drug partnership deals being done with the selected drug, to provide the user with a complete picture of the business and drug research and development landscape. The present invention utilizes a series of algorithms and visualization tools to help the user identify which companies and which drugs the user's company should be interested in acquiring or entering into licensing or research agreements with and will let the user screen, comment on, filter, and collaborate with other users in researching, evaluating, and making decisions on the information.

As mentioned above, many available data sources of interest in this field produce unstructured data. There are known methods for analyzing, processing, and indexing unstructured data. In one embodiment of the invention, Thomson Reuters ATLAS is used for analyzing and indexing unstructured data. For example, U.S. patent application Ser. No. 13/046,266, filed Mar. 11, 2011, and entitled AUTOMATIC DATA CLEANING FOR MACHINE LEARNING CLASSIFIERS, which claims priority to U.S. Provisional Pat. App. No. 61/445,236 filed Feb. 22, 2011, describes systems and techniques for improving the training of machine learning classifiers. U.S. patent application Ser. No. 13/097,619, filed Apr. 29, 2011 and entitled REPRESENTING INFORMATION FROM DOCUMENTS, describes systems and techniques for representing information included in unstructured text documents into a structure format. U.S. patent application Ser. No. 13/107,665, filed May 13, 2011, and entitled ASSOCIATION SIGNIFICANCE, which claims priority to U.S. Provisional Pat. App. No. 61/445,236 filed Feb. 22, 2011, describes systems and techniques for determining the significance between entities. U.S. patent application Ser. No. 13/213,324, filed Aug. 19, 2011, and entitled ENTITY FINGERPRINTS, which claims priority to U.S. Provisional Pat. App. No. 61/445,236 filed Feb. 22, 2011, U.S. Provisional Pat. App. No. 61/486,098 filed May 13, 2011, and U.S. Provisional Pat. App. No. 61/519,592 filed May 25, 2011, describes systems and techniques for exploring relationships among entities. All of the references cited above are incorporated by reference herein in their entirety.

In one embodiment, the invention provides a Business Development & Licensing ("BD&L") system, e.g., implemented both as part of the Thomson Reuters Cortellis intelligence tool, and via an Application Programming Interface ("API") that enables customers to use the results of analyses in other systems. The invention, e.g., when integrated with a system such as the Cortellis system, provides a competitive intelligence system or tool ("CIS") with access to databases of drug pipelines, drug licensing and deals, patents, companies, and archived and current pharmaceutical industry news, along with information on the targets and pathways of disease, and on financial information about the companies developing drugs, and the funding of those companies. CIS provides an intuitive and accessible search interface that provides rapid filtering options, advanced analytic tools, and flexible packaging options. CIS allows for any one keyword search in an intelligence area to be displayed by relevancy and filtered according to user preferences. CIS when offered, for example, with Cortellis is offered as Cortellis for Competitive Intelligence, Clinical Trials Intelligence, Regulatory Intelligence, Decision Support, Informatics, and Information Integration products. The intelligence areas provided in Cortellis include Targets, Drugs, Patents, Companies, Deals, Meetings, Clinical, and Regulatory. Cortellis includes visual analytical tools to assess the competitive intelligence contained within it. One embedment of this invention will be to commercialize the analytical decision support tools that are included in it as additional Cortellis analytics.

In one embodiment of the invention, data is presented to the user through analytics. Visual representations of drugs under consideration and what level of consideration has been given to the drugs by various sources can be shown by color coding the drugs for easy comparison. This information can be combined with information from a user's own drug development pipeline and from records a user's company tracks in a database of possible acquisitions or licensing deals they have considered or are actively tracking, and the three datasets can be overlaid to create a complete picture of all drugs under consideration that are associated with a particular disease target, disease, or drug pathway. Other visual representations will aid the user in finding and relating disease targets, drugs, deals, technologies, companies, and company financings. The visual tools can show drugs, deals, patents, publications and financing related to a selected drug or disease target and the user can choose how to weight or "repaint" the diagram to based on a set of criteria including types of funding, stage of development, and other factors. In one embodiment the visualizations are driven by a program like TIBCO® Spotfire® visualization tools.

In one embodiment of the invention, the data and algorithms are made available to users in the form of an Application Programming Interface (API), for example a Web Services API. Users can submit queries based on drugs, targets and organizations and retrieve information about potential BD&L opportunities in a textual format, for example XML or JSON, as images of the visualization or in coordinate representation that can be explored in third party tools like CytoScape.

In one embodiment, the present invention provides a computer implemented method for identifying a factor associated with a medical issue. The method identifies a set of assets associated with the disease based upon a set of customizable factors. The set of customizable factors being associated with a user-selected set of weighting factors and comprising a set of scientific factors and a set of business factors, the set of customizable factors including one or more from the group consisting of: drug pipeline data; data on drugs in development; a set of financial metrics associated with a set of companies associated with the medical issue; a set of investment data related to the set of companies; and the relevance of various biological targets and the drugs in development against them to the area of focus. The system further provides a manipulatable representation of the set of assets.

In a second embodiment the invention provides a computer-based system comprising: a server comprising a processor adapted to execute code and a memory for storing executable code; a first identification module configured to identify a factor associated with a medical issue; a second identification module configured to identify a set of assets associated with the disease based upon a set of customizable factors, the set of customizable factors being associated with a user selected set of weighting factors and comprising a set of multiple scientific factors and a set of multiple business factors, the set of customizable factors including one or more from the group consisting of: drug pipeline data; data on drugs in development; a set of financial metrics associated with a set of companies associated with the medical issue; a set of investment data related to the set of companies; and the relevance of various biological targets and the drugs in development against them to the area of focus; and a representation module configured to generate for presentation by a display associated with a user access device a manipulatable representation of the set of assets.

In addition, the system may be further characterized as follows. The set of assets (wherein assets may include entities) may further be used to identify a second set of assets. The second set of assets includes existing drug pipeline data, existing financial information, existing disease and disease target research, news, company websites, blogs, conferencing databases, papers, patents, institutions conducting research on the assets or areas of specialization surrounding them, people identified as experts on the first set of assets, results and presentations from scientific conferences, registration documents filed with the FDA, papers in peer reviewed journals, and clinical trials registries. The manipulatable representation comprises a comparison of an asset from the set of assets with another asset from the second set of assets. The factor is at least one of a disease, a condition, a gene, and a protein. The manipulatable representation is a visual representation, and the visual representation is selected from among a target grid population, a target graph, a target map and a target list. The visual representation is also manipulatable by at least one of a company attribute and a drug attribute. The company attribute is at least one of a company type, a funding type, a deal type, and a company history. The drug attribute is at least one of an indication, an action, a development status, a technology, an existing partnership, and an indication of whether the user's company has previously assessed the drug. The set of multiple scientific factors comprises at least one of drug, drug molecule type, drug development status, related patents, drug licensing deals, drug licensing partnerships, clinical trials, FDA decisions, other regulatory body decisions, disease targets, and drug pathways. The set of multiple business factors comprises at least one of partnership status, organization type, publication maturity, target similarity, licensing activity, mergers and acquisitions activity, financial metrics, sales forecasts, private equity funding, existing contracts, types of funding, and prior or current assessment by the user's company. The set of assets comprises at least one of a company, a partnership and a set of rights. The set of rights comprises at least one of a license a license, assignment, contract, and sale.

BRIEF DESCRIPTION OF THE DRAWINGS

In order to facilitate a full understanding of the present invention, reference is now made to the accompanying drawings, in which like elements are referenced with like numerals. These drawings should not be construed as limiting the present invention, but are intended to be exemplary and for reference.

DETAILED DESCRIPTION OF THE INVENTION

The present invention will now be described in more detail with reference to exemplary embodiments as shown in the accompanying drawings. While the present invention is described herein with reference to the exemplary embodiments, it should be understood that the present invention is not limited to such exemplary embodiments. Those possessing ordinary skill in the art and having access to the teachings herein will recognize additional implementations, modifications, and embodiments, as well as other applications for use of the invention, which are fully contemplated herein as within the scope of the present invention as disclosed and claimed herein, and with respect to which the present invention could be of significant utility.

In accordance with the exemplary embodiments described herein, the present invention provides a Business Development & Licensing and Competitive Intelligence System (BD&L/CI, collectively "CIS"), and related methods, adapted to search, aggregate, index, and present data as manipulatable visual representations.

FIGS. 1a through 1d illustrate exemplary structural components and framework for carrying out the present invention and for providing an effective interface for user interaction with such a computer and database-based system. Following that are more detailed descriptions of the implementation of the processes and features of the present invention.

Figure 1A:
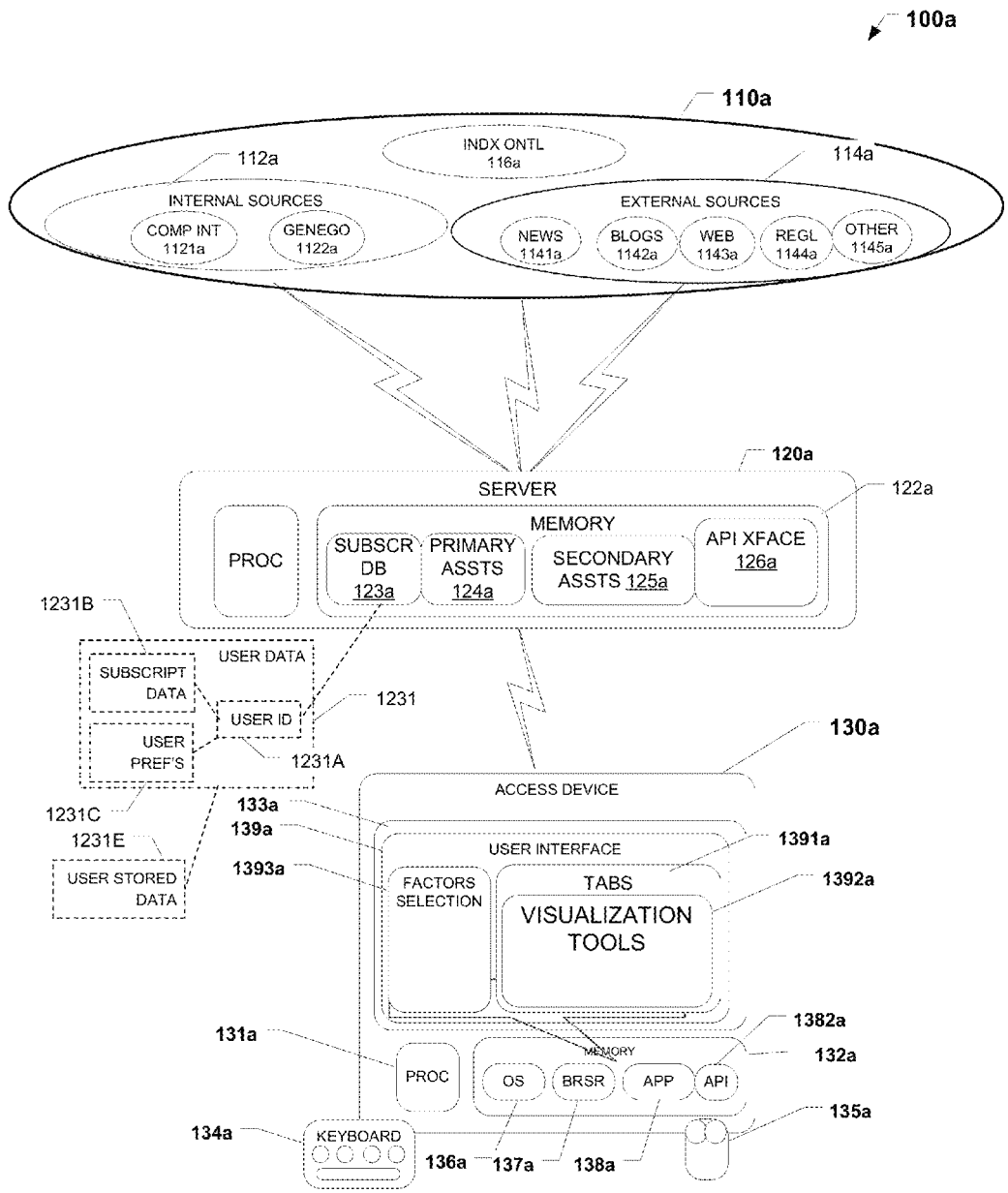
FIG. 1a is a block diagram illustrating one embodiment of the Business Development & Licensing and Competitive Intelligence (BD&L/CI) system architecture according to the present invention.

With reference now to FIG. 1a, an exemplary BD&L-enhanced CIS system 100a comprising an online information-retrieval system adapted to integrate with either or both of a central service provider system or a client-operated processing system is depicted. In this exemplary embodiment, BD&L System 100a includes at least one web server that can automatically control one or more aspects of an application on a client access device, which may run an application augmented with an add-on framework that integrates into a graphical user interface or browser control to facilitate interfacing with one or more web-based applications. System 100a includes one or more databases 110a, one or more servers 120a, and one or more access (e.g., client) devices 130a.

In one implementation, the present invention is incorporated into the Thomson Reuters Cortellis system. As illustrated in FIG. 1a, the BD&L/CI enhanced Cortellis system 100a includes database 110a, server 120a and user interface 139a. In this embodiment, the present invention combines the many separate data sources and services provided by Cortellis into a single platform for providing users with decision support tools to aid in identifying product development, acquisition, licensing opportunities, and competitive intelligence monitoring functions in, for example, a scientific area such as the pharmaceutical and biopharmaceutical areas. As part of the Cortellis system, the present invention combines data and resources for competitive intelligence, clinical trials intelligence, regulatory intelligence, decision support, informatics, and information integration functionality as well as other internal and external data sources.

In this implementation, the invention provides a comprehensive Competitive Intelligence System ("CIS"). CIS allows a user to identify gaps in the market, find a market partner at the right time, compare and view other industry deals, discover targets with active patenting activities, research and evaluate competitor pipelines, and review a company's strategic portfolio. These features are provided by combining information from sources and products, e.g., Thomson Reuters Pharma and Thomson Reuters Partnering. The CIS provides a full picture of the competitive landscape from a single source by combining information from an extensive database of drug pipeline, deals, patents, company content, and the latest industry news. The CIS provides reports such as drug reports, reported and predicted sales figures for all drugs, company reports, deal reports, and patent reports. It also allows for the analysis of any data from within any results set. The CIS provides companies with high quality, real-time data for evidence based decisions, intuitive search-engine-like searches that quickly deliver relevant information, and save time by displaying information in context through analytics and visualizations. The clinical trials intelligence component of the CIS provides information for evaluating market opportunities, identifying potential barriers, and making better informed decisions regarding clinical trial design and operations. The clinical trials intelligence component includes global clinical trial protocols and outcomes for drugs, medical devices and biomarkers that have been uncovered and unified from a variety of data sources. It further includes information from the drugs, deals and patents content to provide insights to support strategic decision making The clinical trials intelligence component supports searching, alerting and exporting capabilities, dynamic real-time visualizations, access to data via APIs, and integration with other commercially available software and solutions. The regulatory intelligence component of the CIS is powered by, for example, the Thomson Reuters IDRAC regulatory intelligence solution. The regulatory intelligence component combines global regulatory information to allow the user to make informed, fast decisions. It provides users with up-to-date regulatory intelligence and analysis that can be used to track regulatory changes, understand submission routes and local practices, compare regulatory requirements, compare existing and emerging competitive products, and learn from regulatory precedence. The information is provided in the form of regulatory intelligence reports, regulatory summaries, reference documents, and global regulatory comparisons. The decision support component of the CIS helps the user see the connections, patterns and relationships between ideas, facts and statistics. The information provided by the decision support component is displayed in a series of dashboards including clinical oncology dashboards. The dashboards can include a trial duration viewer, a portfolio viewer, a drug safety viewer, a disease area viewer, and drug program viewer. The decision support component also provides tools such as virtual merger which allows a user to see how well companies and their drug pipelines align. All of the tools in decision support allow for the identification of patterns and trends through the visualization of data. The visualizations may be driven by, for example, TIBCO® Spotfire® visualization tools. The informatics component of the CIS provides a series of Application Programming Interfaces ("APIs") which access data from the CIS and integrate the information into existing systems. The APIs include analytics, clinical, investigational drugs, ontologies, patents, targets, drug design, and regulatory. The APIs allow a user to gain access to additional information and functionality without changing their existing systems. The informatics component allows internal data to be "mashed up" with proprietary and/or third party data in real time to be used in the CIS platform and APIs. The information integration component of the CIS integrates, aligns, and delivers disparate internal and external competitive intelligence information so that it can be shared across enterprise systems securely and consistently. The information integration component enables the secure hosting of proprietary content, public information and internal data on the CIS platform and can be tailored to meet a company's needs.

There are numerous information areas of Life Sciences content available in the CIS. The targets area allows a user to identify information about precedented targets and their roles in pathological pathways, identify and understand more about a given target or targets, associated with a disease, and identify new opportunities for drug development with an indicated target. The drugs area allows for access to a comprehensive source of drug profiles which enables the visualization of a drug product in the competitive landscape and market at large. drugs also allows a user to see other targets, compounds or drugs in a therapy area and explore research and development options. The patents area allows users to assess patent information to look for IP opportunities, active targets being patented, and find organizations associated with key patents. The companies area allows a user to quickly and easily access full profiles of competitors or potential partners. Further, the companies area allows a user to get a snapshot of a particular company's key contacts, agreements, and financial information. The deals area lets a user explore all deals for a particular target class and benchmark activities against the market while developing an understanding of which companies value a specific drug target. The meetings area allows a user to review conference reports from around 300 conferences and meetings each year and includes summaries and highlights. Conference presentations summarize particular posters and presentations for a number of meetings per year. The clinical area allows a user to analyze the later stages of a compound's development or activity in a specific therapy area or region with the clinical trials intelligence within the CIS. It also allows a user to see the clinical trials landscape in the context of any specific set of activities. Finally, the regulatory area provides a user with the tools to find all the regulatory information necessary to get a drug approved world-wide.

Science and Financial Database 110a includes a set of primary databases (Internal) 112a, a set of secondary databases (External) 114a, and an indexing ontologies module 116a. Primary databases 112a, in the exemplary embodiment, include a Competitive Intelligence database 1121a (in this case represented by exemplary Thomson Reuters Pharma) and a disease targets index database 1122a (in this case represented by exemplary Genego MetaCore). Additional internal sources 112a may include Thomson Reuters Web of Knowledge (WoK) and Web of Science (WoS), Thomson Reuters Literature, Thomson Reuters Intellectual Property, Thomson Reuters Financial and Risk, Thomson Reuters Grants Database, Thomson Reuters One, Thomson Reuters Legal, Thomson Reuters Tax and Accounting Checkpoint, and Thomson Reuters Street Events. Secondary databases 114a include Thomson Reuters News (such as non-internal) database 1141a, Blogs database 1142a, corporate web sites 1143a, regulatory database 1444a, and other content database(s) 1145a. Additional secondary sources included in secondary database 114a may include conferencing databases, papers, results and presentations from scientific conferences, registration documents filed with the FDA, papers in peer reviewed journals, and clinical trials registries.

Indexing Ontologies module 116a is adapted to define the relationships between sets of data. The module contains sets of aliases and alternate terms that can be used to identify and/or classify, for example, diseases, drugs, technologies, and disease targets. Sets of aliases and alternate terms can include types of diseases and specificity, and disease targets or mechanisms of action. The Indexing Ontologies module 116a provides the indexing and linking of Competitive Intelligence database 1121a and disease targets index database 1122a. The module 116a can be used with either structured or unstructured data. When used on unstructured data, an intelligent indexing and association tool (e.g., Thomson Reuters ATLAS) can be used to structure either freeform or un-indexed data. Furthermore, an indexing engine, such as the Microsoft FAST indexing engine, can be used to load an index or freeform text into the science and financial database 110a. Further text mining functionality can be performed by commercially available software such as Linguamatics' i2E or TEMIS' Luxid.

Databases 110a, which take the exemplary form of one or more electronic, magnetic, or optical data-storage devices, include or are otherwise associated with respective indices (not shown). Each of the indices includes terms and phrases in association with corresponding document addresses, identifiers, and other conventional information. Databases 110a are coupled or couplable via a wireless or wireline communications network, such as a local-, wide-, private-, or virtual-private network, to server 120a.

Server 120a, which is generally representative of one or more servers for serving data in the form of webpages or other markup language forms with associated applets, ActiveX controls, remote-invocation objects, or other related software and data structures to service clients of various "thicknesses." More particularly, server 120a includes a processor module 121a, a memory module 122a, a subscriber database 123a, a primary assets module 124a, secondary assets module 125a, and a user-interface module 126a. Processor module 121a includes one or more local or distributed processors, controllers, or virtual machines. Memory module 122a, which takes the exemplary form of one or more electronic, magnetic, or optical data-storage devices, stores subscriber database 123a, primary assets module 124a, secondary assets module 125a, and interface module 126a. Primary assets in the primary assets module 124a include all internal sources such as competitive intelligence 1121a, targets data or index 1122a and financial data or index (not shown). Secondary assets in the secondary assets module include a user company's drug pipeline data, user financial information, user disease and disease target research, information on which companies and drugs the user's company has considered or is considering acquiring or licensing, news, company websites, blogs, conferencing databases, papers, results and presentations from scientific conferences, registration documents filed with the FDA, papers in peer reviewed journals, and clinical trials registries. API and information-integration-tools (IIT) framework module 126a (or software framework or platform) includes machine readable and/or executable instruction sets for wholly or partly defining software and related user interfaces having one or more portions thereof that integrate or cooperate with one or more applications.

Subscriber database 123a includes subscriber-related data for controlling, administering, and managing pay-as-you-go or subscription-based access of databases 110a. In the exemplary embodiment, subscriber database 123a includes one or more user preference (or more generally user) data structures. In the exemplary embodiment, one or more aspects of the user data structure relate to user customization of various search and interface options stored as user stored data 1231. User data 1231 also includes user ID 1231A, subscription data 1231B, user preferences 1231C, and external user stored data 1231E. Primary assets module 124a includes one or more search engines and related user-interface components, for receiving and processing user queries against one or more of databases 110a.

Still with reference to FIG. 1a, access device 130a, such as a client device, is generally representative of one or more access devices. In the exemplary embodiment, access device 130a takes the form of a personal computer, workstation, personal digital assistant, mobile telephone, or any other device capable of providing an effective user interface with a server or database. Specifically, access device 130a includes a processor module 131a one or more processors (or processing circuits) 131a, a memory 132a, a display 133a, a keyboard 134a, and a graphical pointer or selector 135a. Processor module 131a includes one or more processors, processing circuits, or controllers. In the exemplary embodiment, processor module 131a takes any convenient or desirable form. Coupled to processor module 131a is memory 132a. Memory 132a stores code (machine-readable or executable instructions) for an operating system 136a, a browser 137a, document processing software 138a. In the exemplary embodiment, operating system 136a takes the form of a version of the Microsoft Windows operating system, and browser 137a takes the form of a version of Microsoft Internet Explorer. Operating system 136a and browser 137a not only receive inputs from keyboard 134a and selector 135a, but also support rendering of graphical user interfaces on display 133a. Upon launching processing software an integrated information-retrieval graphical-user interface 139a is defined in memory 132a and rendered on display 133a. Upon rendering, interface 139a presents data in association with one or more interactive control features (or user-interface elements) which is stored in memory as API 1382a.

An exemplary user interface 139a is shown with user interface elements Factors Selection Area 1393a, tabs 1391a, and visualization tools area 1392a. Factors selection area 1393a enables user selection of one or more factors to be used in defining the manipulatable visualization to be display in visualization tools area 1392a. Customizable factors selectable by the user to be used in creating the visualization to be displayed in visualization tools area 1392a include companies, drugs, drug molecule type, drug development status, related patents, drug licensing deals/ partnerships, clinical trials, FDA/other regulatory body decisions, disease targets, drug pathways, partnership status, organization type, publication maturity, target similarity, licensing activity, mergers and acquisitions activity, financial metrics, sales forecasts, private equity funding, existing contracts, types of funding, prior/current assessment by user's company, and other scientific and financial factors. The particular visualization displayed in visualization tools area 1392a can be changed by selecting an option from tabs 1391a. Selectable visualization tools include, but are not limited to, a target grid population, a target graph, a target map, and a target list.

In one embodiment of an operating a system using the present invention, an add-on framework is installed and one or more tools or APIs on server 120a are loaded onto one or more client devices 130a. In the exemplary embodiment, this entails a user directing a browser in a client access device, such as access device 130a, to internet-protocol (IP) address for an online information-retrieval system, such as offerings from Thomson Reuters Cortellis and other systems, and then logging onto the system using a username and/or password. Successful login results in a web-based interface being output from server 120a, stored in memory 132a, and displayed by client access device 130a. The interface includes an option for initiating download of information integration software with corresponding toolbar plug-ins for one or more applications. If the download option is initiated, download administration software ensures that the client access device is compatible with the information integration software and detects which document-processing applications on the access device are compatible with the information integration software. With user approval, the appropriate software is downloaded and installed on the client device. In one alternative, an intermediary "firm" network server may receive one or more of the framework, tools, APIs, and add-on software for loading onto one or more client devices 130a using internal processes.

Once installed in whatever fashion, a user may then be presented an online tools interface in context with a document-processing application. Add-on software for one or more applications may be simultaneous invoked. An add-on menu includes a listing of web services or application and/or locally hosted tools or services. A user selects via the tools interface, such as manually via a pointing device. Once selected the selected tool, or more precisely its associated instructions, is executed. In the exemplary embodiment, this entails communicating with corresponding instructions or web application on server 120a, which in turn may provide dynamic scripting and control of the host word processing application using one or more APIs stored on the host application as part of the add-on framework.

Figure 1B:
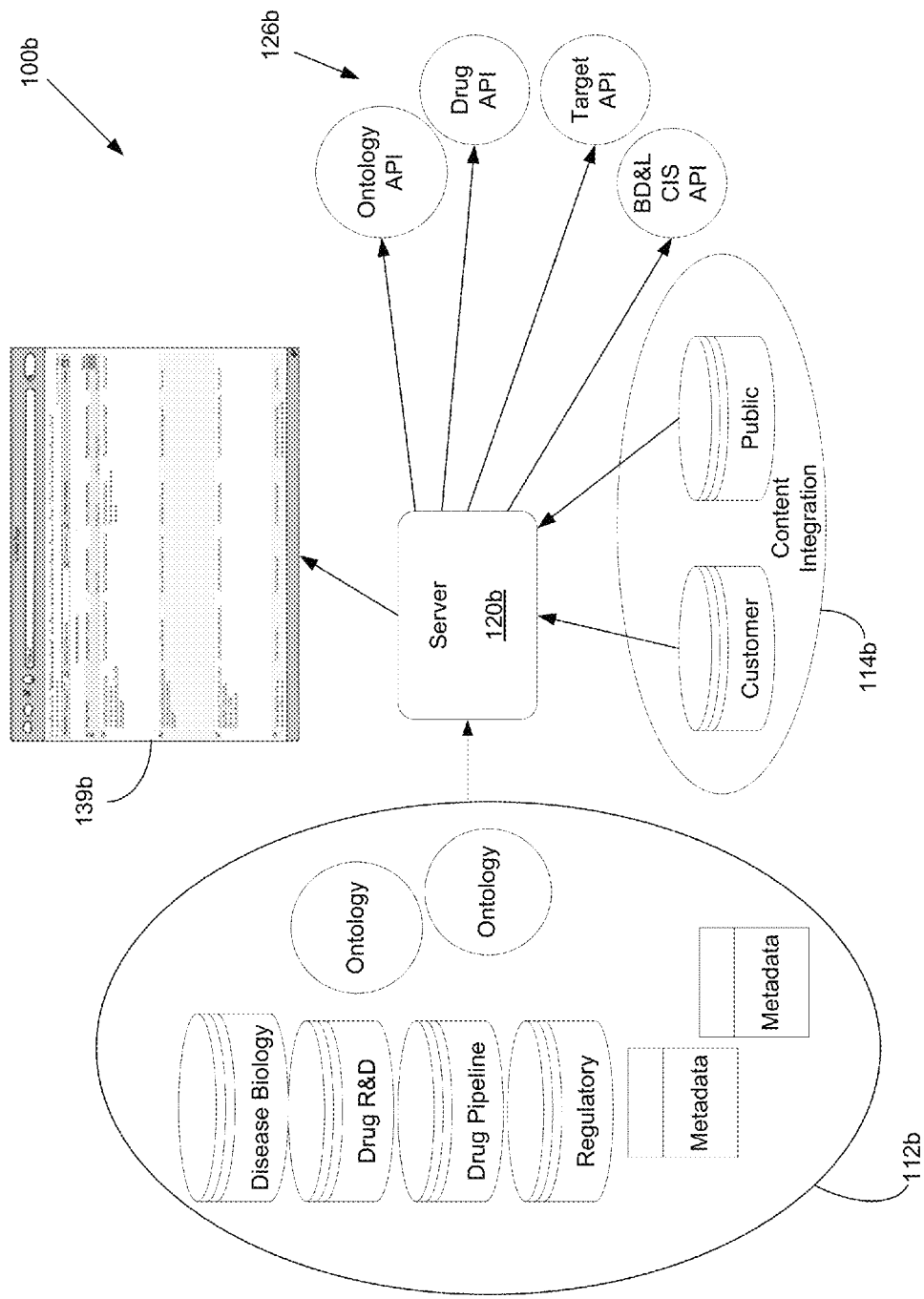
FIG. 1b is a block diagram illustrating one embodiment of the BD&L/CI system architecture according to the present invention.

With reference now to FIG. 1b, another exemplary embodiment of the system is depicted. System 100b comprises internal database 112b, external database 114b, server 120b, APIs 126b, and user interface 139b. The internal database 112b is consists of, for example, databases for disease biology, drug R&D, drug pipelines, regulatory information, metadata, and ontologies indexes. External database 114b consists of, for example, both customer controlled databases and public databases that have been integrated or indexed together such that they can be accessed as a single data source by server 120b. The server 120b presents a user interface 139b to the user to enable search functionality, visualizations, analytics, and general system interaction. The server 120b may also be configured to direct the data to one or more APIs such as an ontology API, a drug API, a target API, or a BD&L/CI API.

Figure 1C:
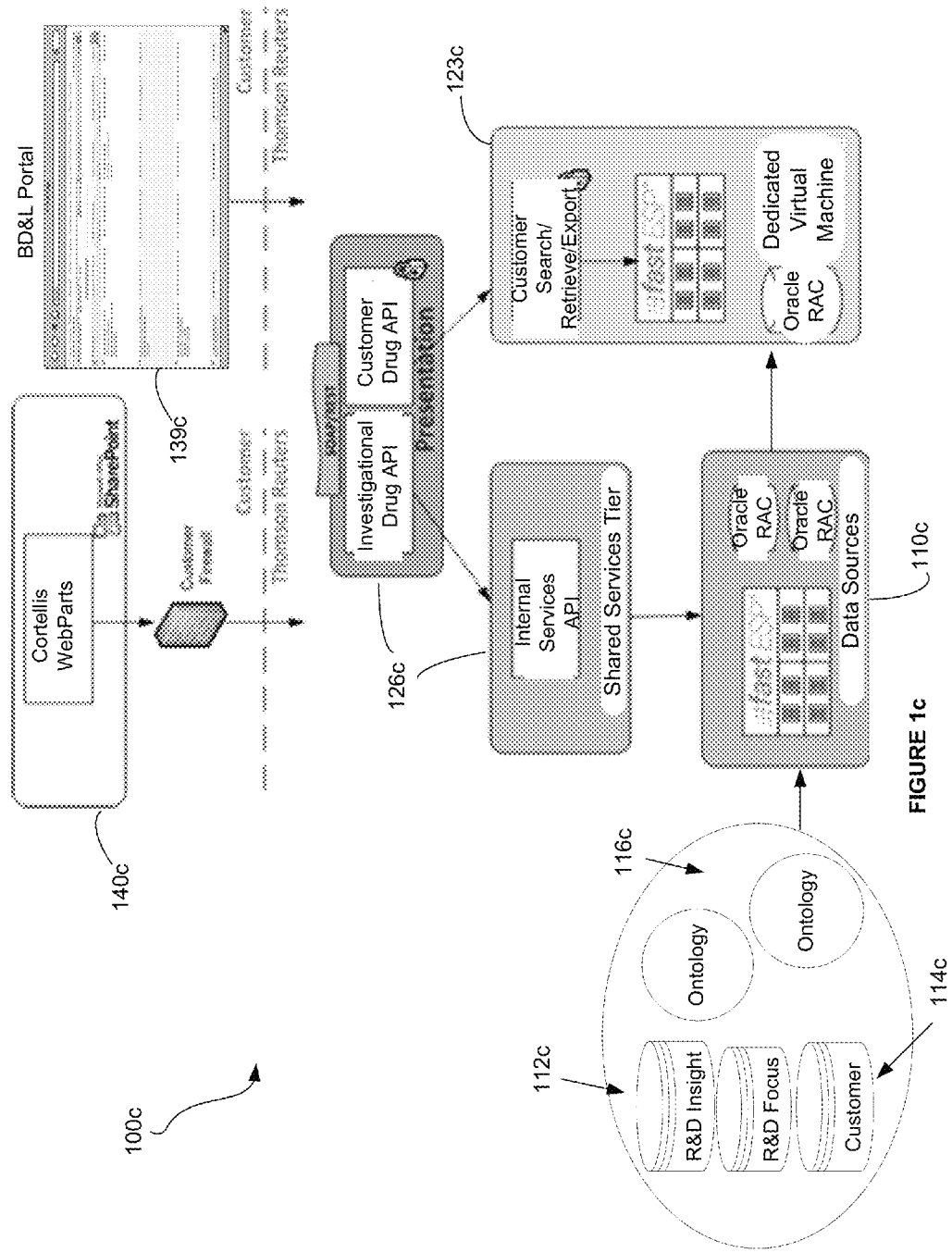
FIG. 1c is a block diagram illustrating one embodiment of the BD&L/CI system architecture according to the present invention.

With reference now to FIG. 1c, another exemplary embodiment of the system is depicted. System 100c comprises database 110c, internal database 112c, external database 114c, ontologies indexes 116c, subscriber database 123b, API/IIT interface 126c, user interface 139c, and integration component (in this example Cortellis WebParts through Microsoft Office SharePoint) 140b. Databases 112c, 114c, and ontologies indexes 116c are indexed and stored in database 110c. The indexing is performed by the Microsoft FAST indexing and searching service, and the database 110c is managed by a DBMS such as Oracle RAC. Access to the information on database 110c is controlled by subscriber database 123b. The subscriber database 123b also controls user options, user searches, user search results, and user export features. The API/IIT interface 126c comprises a shared services tier and a presentation tier. The shared services tier is accessed through an internal services API. The data is presented to the user through the presentation tier and, for example, the investigation drug API or customer drug API. The user directly interacts with system 100c through user interface 139c which is, for example, a web interface displayed in a web browser such as Microsoft Internet Explorer.

Figure 1D:
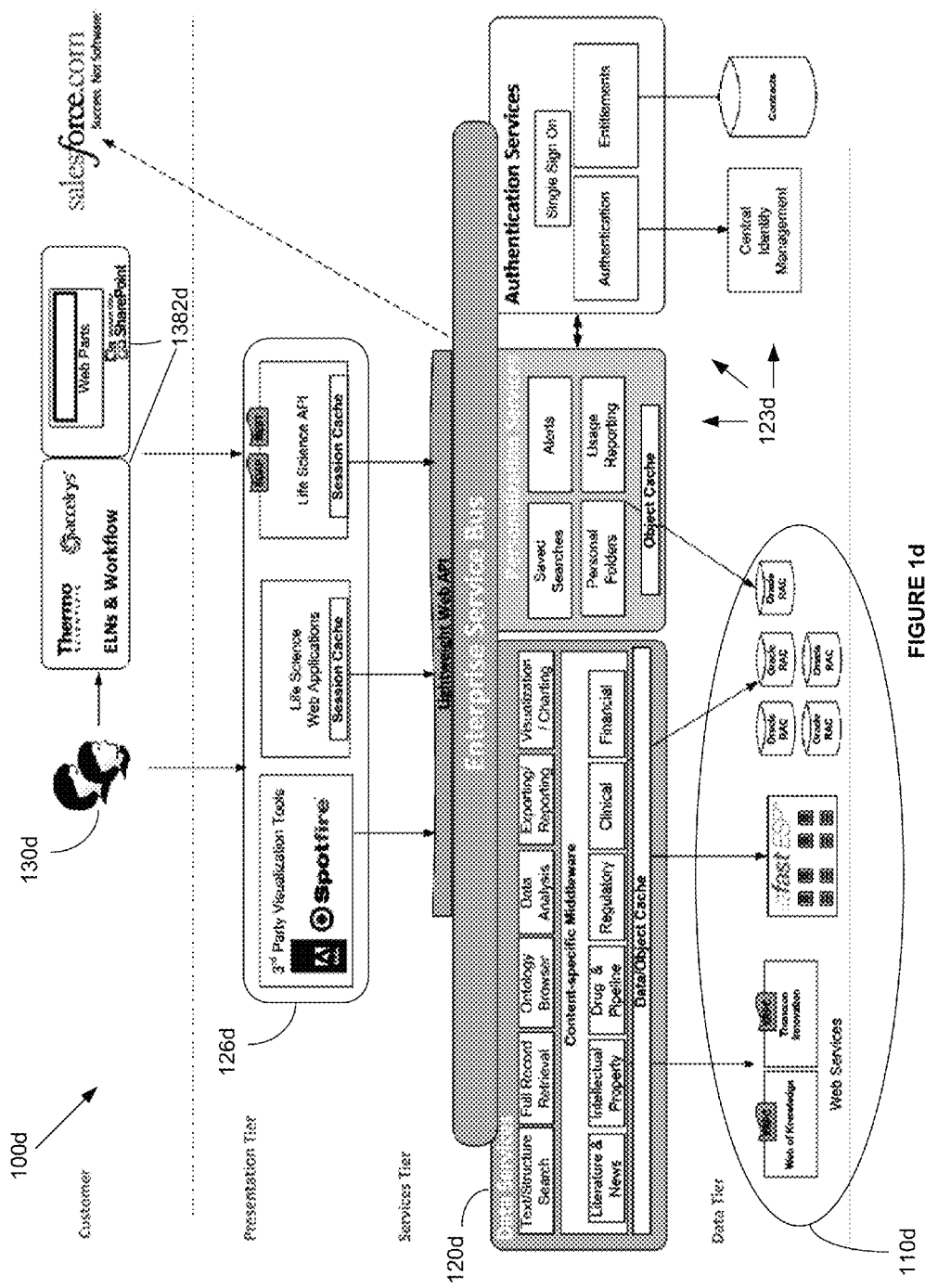
FIG. 1d is a block diagram illustrating one embodiment of the BD&L/CI system architecture according to the present invention.

With reference now to FIG. 1d, another exemplary embodiment of the system is depicted. In system 100d, access to the server 120d is presented through a web-based API and is controlled by an enterprise service bus. The server 120d comprises data services, content-specific middleware, and a data/object cache for communication with database 110d. Data services provided by the server 120d include, for example, text/structure search, full record retrieval, ontology browser, data analysis, exporting/reporting, and visualization/charting. The content-specific middleware is adapted to handle specific content types, e.g., literature & news, intellectual property, drug & pipeline, regulatory, clinical, and financial. Directly connected to server 120d is subscriber management system 123d. The subscriber management system 123d comprises both personalization services and authentication services to control access to the system 100d and to provide user customization of the interface and services. Personalization services include, for example, saved searches, alerts, personal folders, and usage reporting. The personalization services provided by subscriber management system 123d allow the user to customize their interactions and facilitate an enhanced user experience. Access to the system 100d is managed by the authentication services features of subscriber management system 123d. The authentication services provided by subscriber management system 123d allow for authentication, entitlements/provisioning, and single sign on functionality for access to all the features provided by server 120d. The information, tools, visualizations, analytics, and services provided by the system 100d are presented to the user system 130d through API/IIT interface 126d. The interface 126d is adapted to present the functionality of server 126d through tools such as TIBCO Spotfire, Life Science Web Applications, and the Life Science API. The APIs managed by interface 126*d* are stored and accessed on user system 130*d* as APIs 1382*d*.

FIGS. 2 through 5 depict a series of example manipulatiable visual representations that can be provided by the system. The particular representations depicted are shown for illustrative purposes only, and are not intended to be limiting on the claimed invention. The representations may be one of a target or entity grid population, a target or entity graph, a target or entity map, and a target or entity list, where a target or entity is a disease target or other area of drug type/focus, drug or company. Furthermore, the set of FIGS. 2 through 5 all relate to a single exemplary case wherein a user has selected a set of customizable factors and has chosen what weight to assign to each factor in the set of factors. Each of FIGS. 2 through 5 depicts a different manipulatable visual representation or "visualization" of the data identified, retrieved, and processed by the system using the selected factors.

Figure 2:
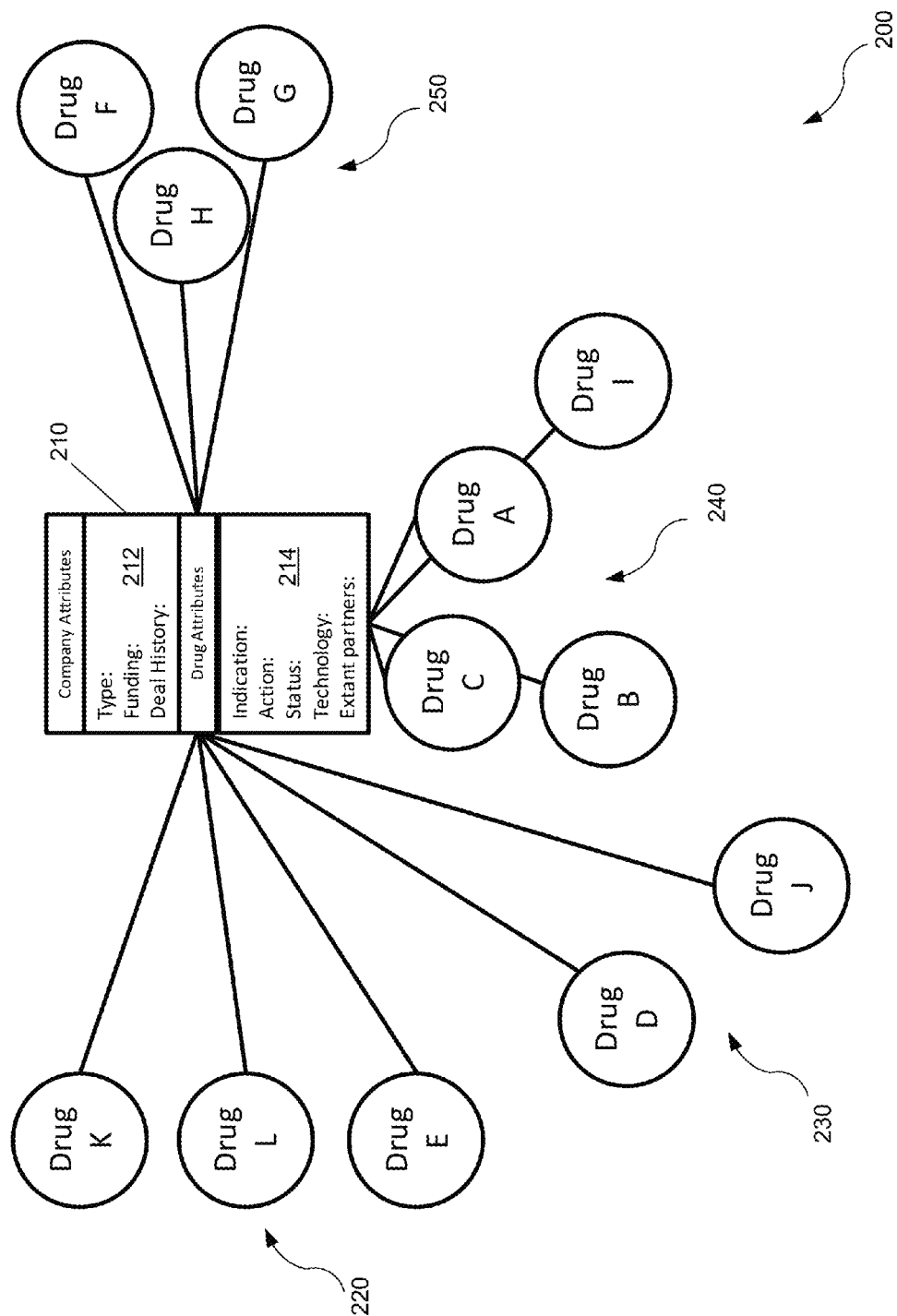
FIG. 2 illustrates an exemplary representation of a visualization of data collected by the present invention based on user specified factors.

With reference now to FIG. 2, a target map 200 is shown which depicts the fit, or relative relatedness or degree of matching of a set of drugs to a set of selected customizable factors which were selected by a user. The weight assigned to the factors was also determined by the user to customize the target map 200. Factors area 210 lists the set of customizable factors selected by the user. Business factors 212 lists the customizable business factors that were selected by the user and used in rendering the target map 200. Drug attributes 214 lists the customizable drug factors that were selected by the user and used in rendering the target map 200. The factors shown may be further customized or selected via drop down boxes or range sliders in factors area 210. The distance of each drug on target map 200 from the factors area 210 gives the user instant visual information as to how close a fit each drug is to an ideal drug candidate. The positioning of the drugs in the target map, and (although not shown in this example) the color coding and size of the circles, are generated based on the fit of the drugs to the user's preferences. They are calculated using measurements of the various factors. Drugs that are closer to the ideal drug fingerprint appear closer to the idea drug specified in factors area 210 and are clustered by shared attributes. The distance to factors area 210 changes as the parameters for business factors 212 and drug attributes 214 for the ideal drug are altered. The drug cluster 220 comprises drugs that are a good fit according to the drug factors but would be challenging to acquire in a deal due the company profile of the company that owns the drugs. The drug cluster 230 comprises drugs that are less of a good fit than those of cluster 220 because their drug actions are not in the user specified drug pathway. The drug cluster 240 comprises drugs that are closest in fit to the ideal drug candidate. The drugs comprising cluster 240 share an action, indication, technology terms, and commercial attributes with the ideal drug specified in factors area 210. The drugs in cluster 250 appear further from factors area 210 than those of cluster 240 because although they share some factors, indication and technology, their action is different, though in the same pathway. The positioning of the drugs in the target map, and (although not shown in this example) the color coding and size of the circles, are generated based on the fit of the drugs to the user's preferences. They are calculated using measurements of the various factors.

Figure 3:
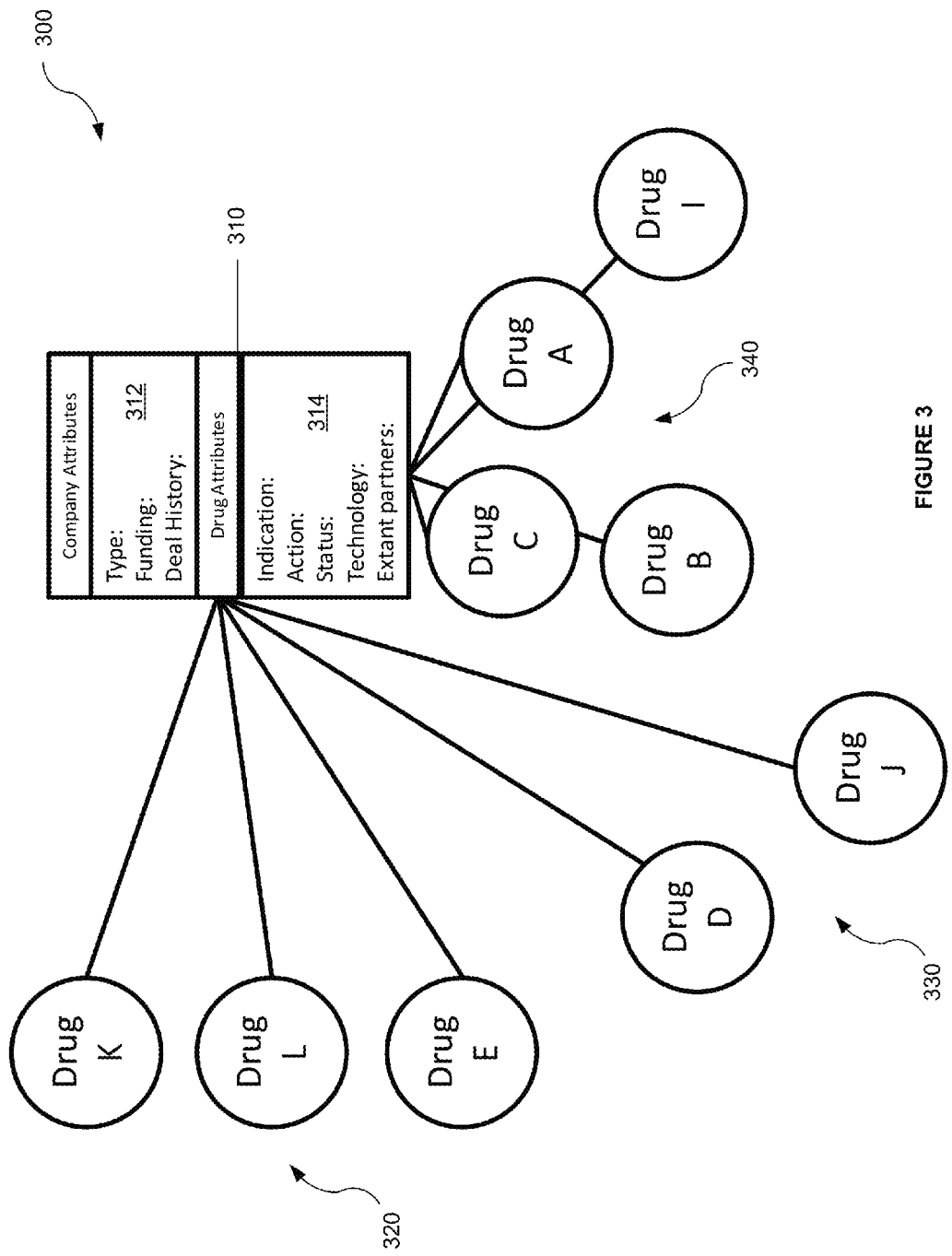
FIG. 3 illustrates an exemplary representation of a visualization of data collected by the present invention based on user specified factors.

With reference now to FIG. 3, a target map 300 is shown which depicts the fit, or relative relatedness or degree of matching of a set of drugs to a set of selected customizable factors which were selected by a user. FIG. 3 depicts the same set of data retrieved and displayed in FIG. 2, but in FIG. 3 the user has chosen to exclude from the visual representation any drugs whose drug actions are not the same as the drug action specified by the user. The weight assigned to the factors was also determined by the user to customize the target map 300. Factors area 310 lists the set of customizable factors selected by the user. Business factors 312 lists the customizable business factors that were selected by the user and used in rendering the target map 300. Drug attributes 314 lists the customizable drug factors that were selected by the user and used in rendering the target map 300. The distance of each drug on target map 300 from the factors area 310 gives the user instant visual information as to how close a fit each drug is to an ideal drug candidate. The positioning of the drugs in the target map, and (although not shown in this example) the color coding and size of the circles, are generated based on the fit of the drugs to the user's preferences. They are calculated using measurements of the various factors. Drugs that are closer to the ideal drug fingerprint appear closer to the idea drug specified in factors area 310 and are clustered by shared attributes. The factors shown may be further customized or selected via drop down boxes or range sliders in factors area 310. The distance to factors area 310 changes as the parameters for business factors 312 and drug attributes 314 for the ideal drug are altered. The drug cluster 320 comprises drugs that are a good fit according to the drug factors but would be challenging to acquire in a deal due the company profile of the company that owns the drugs. The drug cluster 330 comprises drugs that are less of a good fit than those of cluster 320 because their drug actions are not in the user specified drug pathway. The drug cluster 340 comprises drugs that are closest in fit to the ideal drug candidate. The drugs comprising cluster 340 share an action, indication, technology terms, and commercial attributes with the ideal drug specified in factors area 310.

Figure 4:
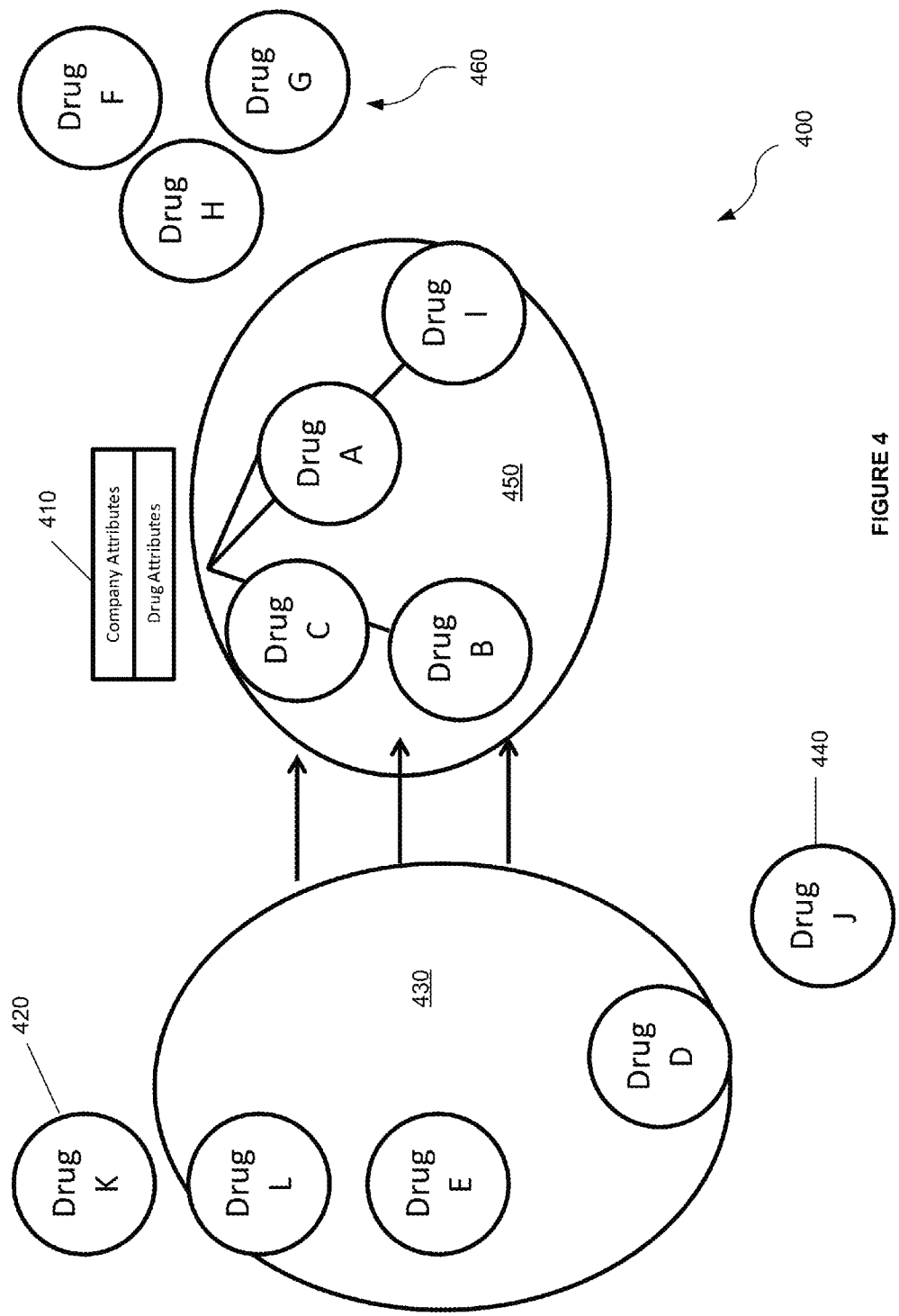
FIG. 4 illustrates an exemplary representation of a visualization of data collected by the present invention based on user specified factors.

With reference now to FIG. 4, a visual representation 400 is shown which depicts the same set of data shown in FIGS. 2 and 3 re-arranged according to the user's selections. The visual representation 400 shows drug clusters 420-460 grouped according to user selected and weighted factors. The factors can be changed or re-weighted by the user by selecting them in factors area 410. Drugs that are closer to the ideal drug fingerprint appear closer to the ideal drug specified in factors area 410 and are clustered by shared attributes. Drugs in cluster 450 are those that are closest in fit to the ideal drug specified by the user selectable factors. Drugs found in cluster 430 are those that are a close fit, but one or more issues prevents them from being and ideal candidate. The positioning of the drugs in the target map, and (although not shown in this example) the color coding and size of the circles, are generated based on the fit of the drugs to the user's preferences. They are calculated using measurements of the various factors. However, drugs in cluster 430 may be moved into cluster 450 if their problems could be resolved. Drugs 420 and 440 may be similar in fit to those found in cluster 430, but cannot be moved into the cluster of ideally fitting drugs 450 due to one or more factors. The drugs in cluster 460 may be closer in fit to the factors for the ideal candidate than those found in cluster 430, but all drugs in cluster 460 share a similar flaw that prevents the drugs from being considered as ideal candidate.

Figure 5:
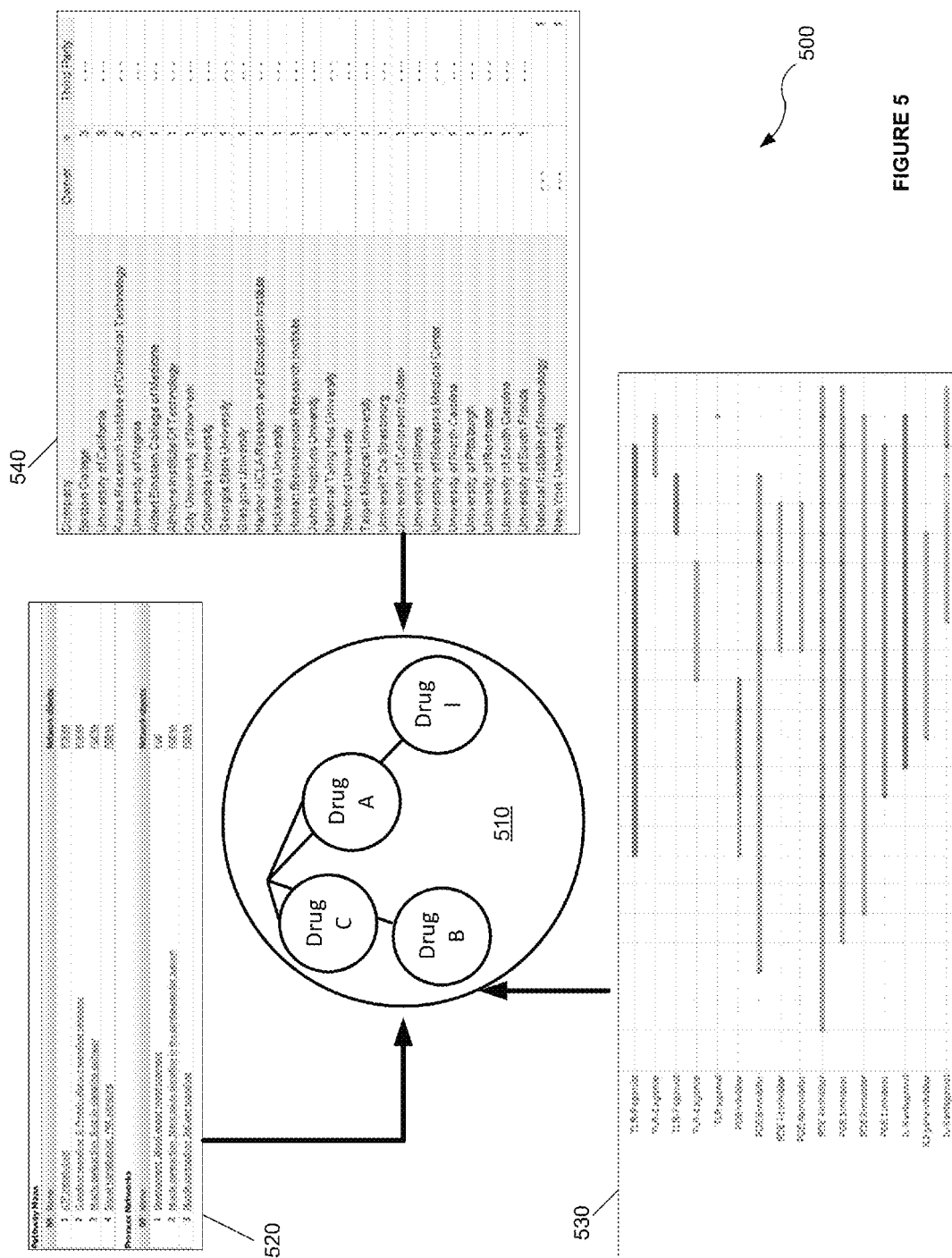
FIG. 5 illustrates an exemplary representation of a visualization of data collected by the present invention based on user specified factors.

With reference now to FIG. 5, a visual representation 500 is shown which depicts examples of the specific data used by present invention in clustering drugs 510 according to the user customized and weighted set of factors. Table 520 is a table of pathway maps and process networks found by the system to be a close fit to the idea drug factor specified by the user. The table 530 lists disease targets and also shows detailed information about the effectiveness and applications of individual disease targets. Table 540 lists institutions or organizations that own intellectual property or that do research related to the disease, disease targets, pathways, or actions specified by the user. The information gathered from these separate data sources is used by the system in determining which set of drugs belongs in the cluster 510 as the closest fit to the specified ideal drug candidate.

Figure 6:
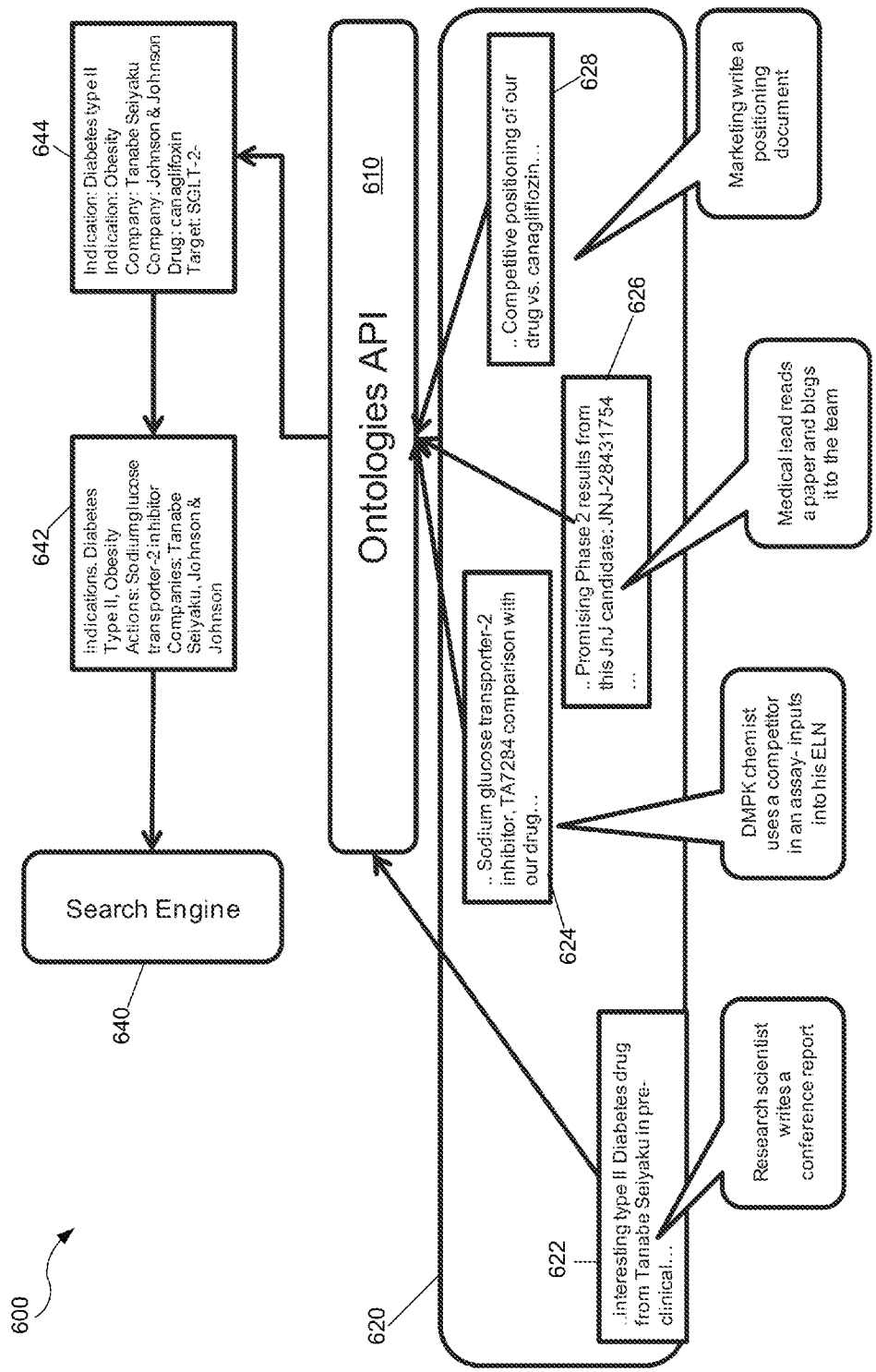
FIG. 6 is a flowchart depicting the process of obtaining information from data sources via the present invention.

With reference now to FIG. 6, a flowchart 600 is shown which depicts an exemplary embodiment of how the Indexing Ontologies module 116 uses aliases and alternate terms to collect and provide information in the present invention as the result of a user search for a drug. FIG. 6 illustrates how the ontologies API/ontologies service allows documents created during performance of normal daily operations of a drug company, for example, can be brought into the CIS system for analysis alongside other data elements in the CIS. In one exemplary manner, the Ontologies API 610 is connected to the internal documents repository 620. Information sources in the documents repository 620 include both internal and external information sources and comprise both scientific and financial information. The information in repository 620 is enriched to enable rapid and accurate searching and collection. In this exemplary embodiment, report 622 is a conference report written by a research scientist, document 624 is an electronic lab notebook (ELN) in which a Drug Metabolism and Pharmacokinetics (DMPK) chemist has used a competitor as an assay input, blog entry 626 is a summary of a paper read by a medical lead, and document 628 is a marketing positioning document. Documents and reports 622-628 were identified because key terms contained in the documents had been indexed and enriched by the Ontologies API 610. Algorithms such as Thomson Reuters ATLAS and indexing tools such as Microsoft FAST Indexing Tool may be employed to index and enrich the documents. The enriched documents are then easily identified in a search by a user. Entity extraction first finds and normalizes the terms in the documents 622-628 and presents them as a summary 644. The summary data 644 is then used to supplement any other data based on existing knowledge of the drug and is presented as enriched summary 642. The enriched summary is them presented to the user as the search results to search engine 640.

Referring now to FIGS. 7 through 10, a series of exemplary screen shots and user interface elements illustrate an embodiment of the invention. FIGS. 7 through 10 illustrate the process of a user researching information about selecting candidates for pharmaceutical company's research collaboration/licensing/acquisition deals with smaller biotechnology companies. The user utilizes the present invention to retrieve targets and visualize information related to disease targets closely related to a "starting" disease in order to make an intelligent decision regarding company strategy. The present invention will provide the user with information on what activities are being undertaken in the disease target area related drugs in development, companies developing them, and investments in those companies and drugs to fund drug development, and will also provide information about similar disease or biologic targets that show promise in the area of interest. For example, EGFR inhibitors versus VEG-F inhibitors as similar biological targets for drugs to treat various forms of cancer. Factors for which drugs show promise include drugs not associated with other companies and drugs not currently in development to treat the primary disease are of focus (e.g., types of cancer), but which are based on a disease or biologic target or pathway that may show promise for the disease area based on its proximity to targets that have shown promise in the disease area. The present invention will also provide the user with information that will show, given the selected disease or biologic target, the companies and institutions with patents tied to the target, drugs linked to the target, and the business and licensing deals done for drugs with the selected target. This information will assist the user in making informed decisions regarding his or her company's business development and licensing strategy, taking into account the company's previous or current consideration of drugs in the area of focus.

Figure 7:
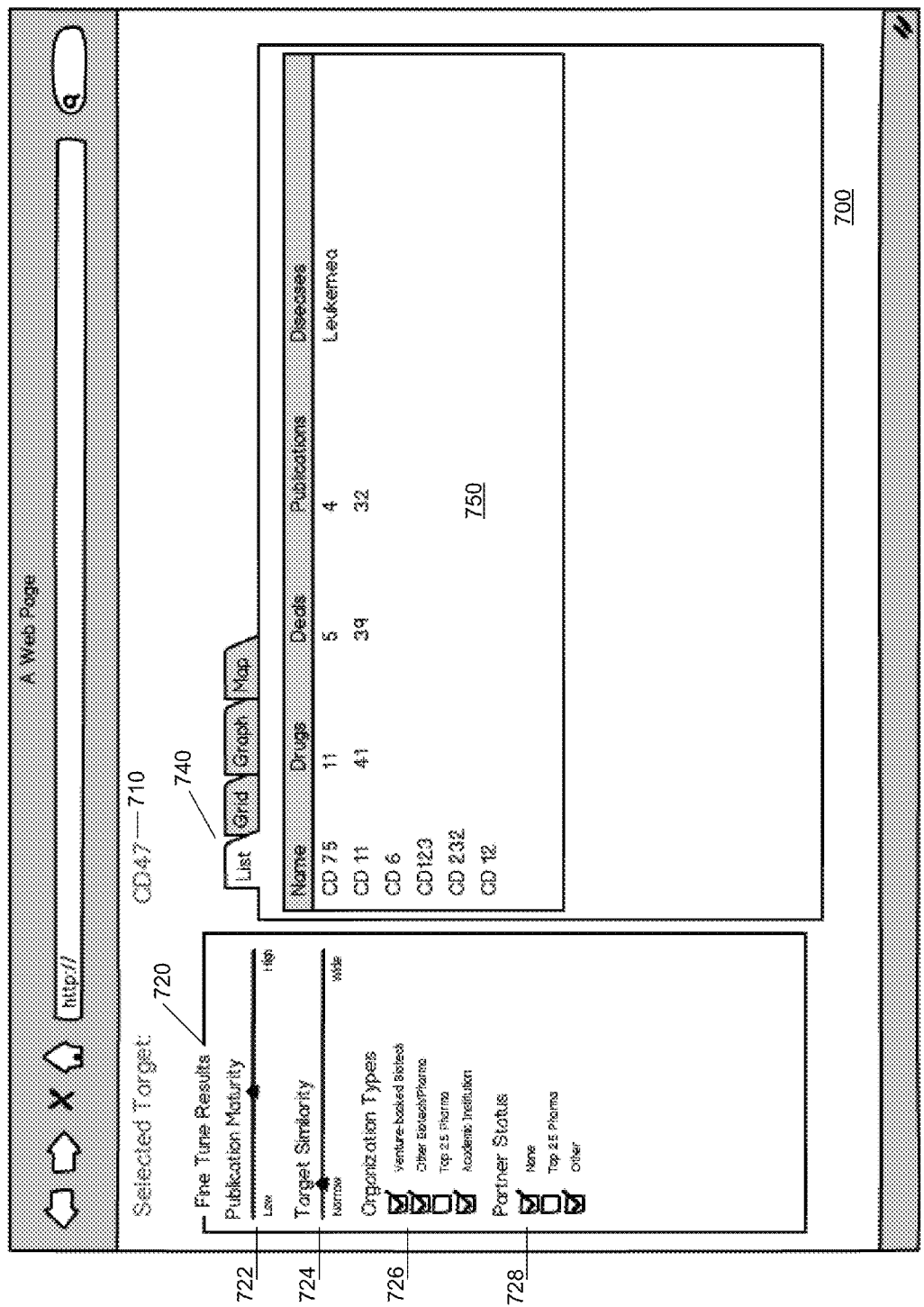
FIG. 7 illustrates an exemplary user interface and a visualization of data collected by the present invention based on user specified factors.

With reference now to FIG. 7, an exemplary user interface 700 is depicted which provides the user with additional options for configuring and viewing a set of disease or biologic targets identified through the user's selection of a specific disease/biologic target 710 and additional factors 722-728. The factors selection area 720 allows the user to further tune the results returned from the initial search. The tuning of the results can be done by the user adjusting the factors to be used in creating the visual representation 750. In this embodiment, publication maturity slider 722, target similarity slider 724, organization type list 726, and partner status 728 may all be used in further adjusting and tuning the data set to be displayed in the visual representation. Other factors may also be used to further tune the results. One such factor is indications for which papers have been published, which patents have been filed, and what drugs are in development against a target. The indications may be reduced by the user from the starting point. Another factor could include more information about the biological targets. The user could choose for the visual representation to show upstream targets, downstream targets, and targets in the same disease pathway. The starting point would be the target the user has initially selected, target 710, but the range of the search may be expanded with a selection slider. Organization type 726 allows the user to select the type of organization that owns or controls a particular drug or is involved in research regarding a particular target. The user may select from venture-backed biotech, other biotech/pharmaceutical organizations, top 25 pharmaceutical companies, or academic institutions. The user may further refine or change the organization types after obtaining the initial results. If the user selects venture-backed biotech for organization type 726, the user will be presented with a funding status slider that will allow the user to choose a date prior to the present date that can be used to narrow or widen the search, for example by filtering out companies that have received recent rounds of funding. The partner status list 728 will initially be unchecked and all drugs that are relevant to the original search initially will be shown. The user may then select partner statuses from the list to filter out organizations that are not partnered at all, partnered with a top 25 pharmaceutical company, or are involved in a different form of partnership. If the "other" option is selected the user will be allowed to further specify the type of partnership to be included. The results of the user's selections in the factors selection area 720 will be used to create a target list 750. The type of visual representation shown can be specified by the user by selecting from the list of tabs 740. In this exemplary embodiment, a target list 750 is shown, listing the targets with the best fit to the user's customized list of factors.

Figure 8:
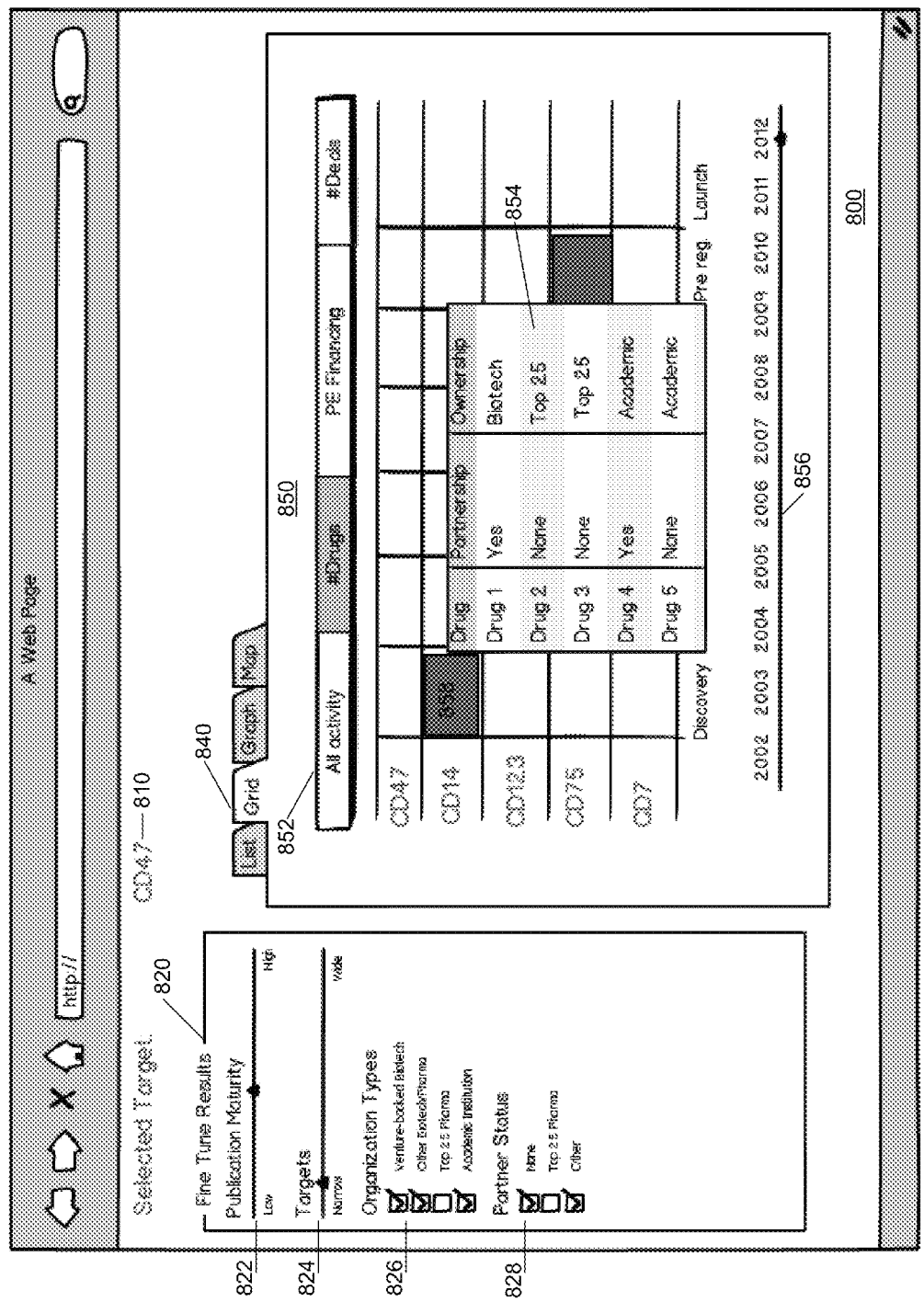
FIG. 8 illustrates an exemplary user interface and a visualization of data collected by the present invention based on user specified factors.

With reference now to FIG. 8, an exemplary user interface 800 is depicted which provides the user with additional options for configuring and viewing a set of biological targets identified through the users selection of a specific target 810 and additional factors 822-828. The data shown in target grid 850 is the same as depicted in list 750. The user has selected the "Grid" option from tab list 840. The user may further manipulate the target graph by selecting from options 852 to reorder or reorganize the target graph. If the user selects a time segment from the target graph 850, a detailed list of information 854 about the target at the selected time segment 858 is displayed. The time segments are broken down and described by the phase of a particular drug related to a disease target, state of drugs in development, attributes of companies developing them, deals and funding to finance their development as of the time specified with the slider. The user may specify the time period to be shown by using the time slider 856.

Figure 9:
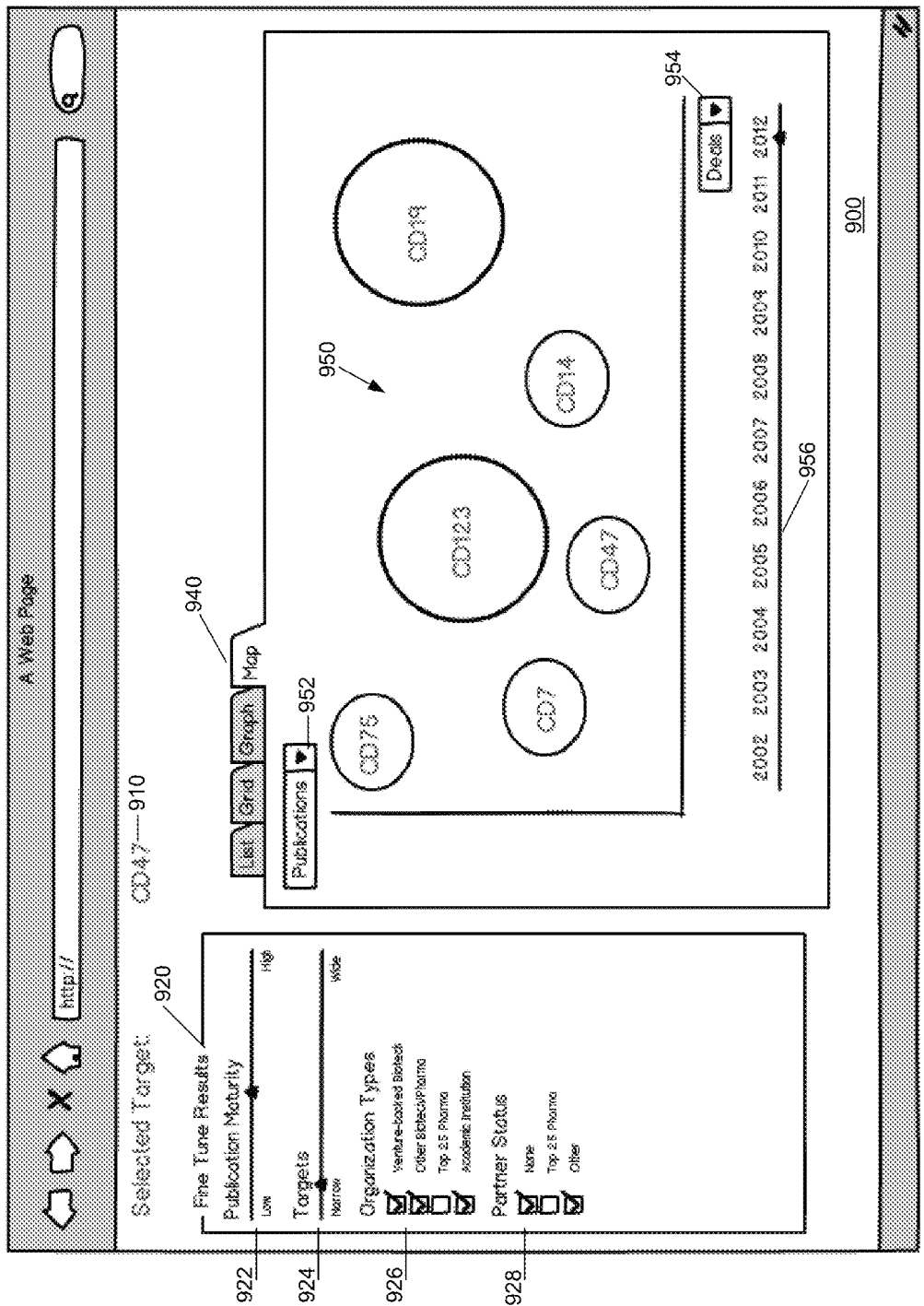
FIG. 9 illustrates an exemplary user interface and a visualization of data collected by the present invention based on user specified factors.
Figure 10:
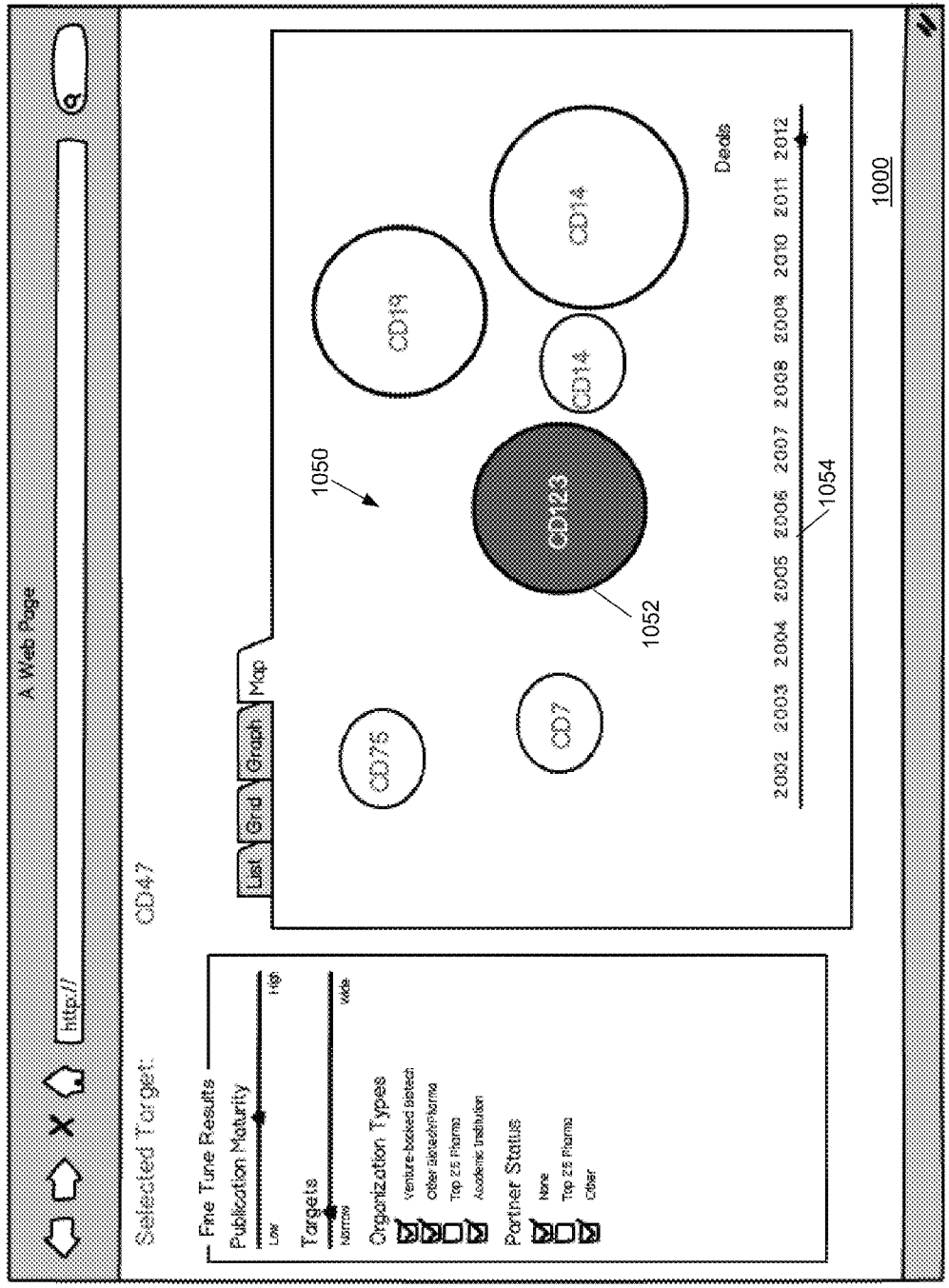
FIG. 10 illustrates an exemplary user interface and a visualization of data collected by the present invention based on user specified factors.

With reference now to FIG. 9, an exemplary user interface 900 is depicted which provides the user with additional options for configuring and viewing a set of biological targets identified through the users selection of a specific target 910 and additional factors 922-928. The data shown in target map 950 is the same as the data depicted in target list 750 and target graph 850 and is a further example of a visualization such as described with reference to FIGS. 2-5 above. In FIG. 9, the user has selected the "Map" option from the tab list 940 and has been presented with target map 950. The targets shown on the target map 950 are shown in a size proportional to the factors selected in drop down boxes 952 and 954. In this example, the user has selected the publications indicator from box 952 and the deals option from box 954, so the positioning of the circle for each target along the X and Y access will be based on the relative number of scientific papers published, and the number of deals that have been made, respectively, for each target. The user may further customize the visualization by selecting the time frame to be shown using time slider 956. The user may also select any of the targets in target map 950 to re-format the chart around the selected target, or, with another option not shown in the figure, the user could choose to select a specific target and re-draw the chart showing drugs in development, deals between companies, publications, patents, etc., instead of targets. With reference now to FIG. 10, the user has selected target 1052 (CD 123) and the representation has be re-configured in response to this selection. The user may further select any other targets from target map 1050 and may select a time frame using time slider 1054 to further customize the representation.

The user can, at any point, save the chart, share it with others, set alerts to be notified of changes to any of the entities (companies, drugs, deals, publications, patents, etc) that are within the scope of the chart. The user can also annotate any of the entities on the chart, saving annotations for private or shared viewing.

Figure 11:
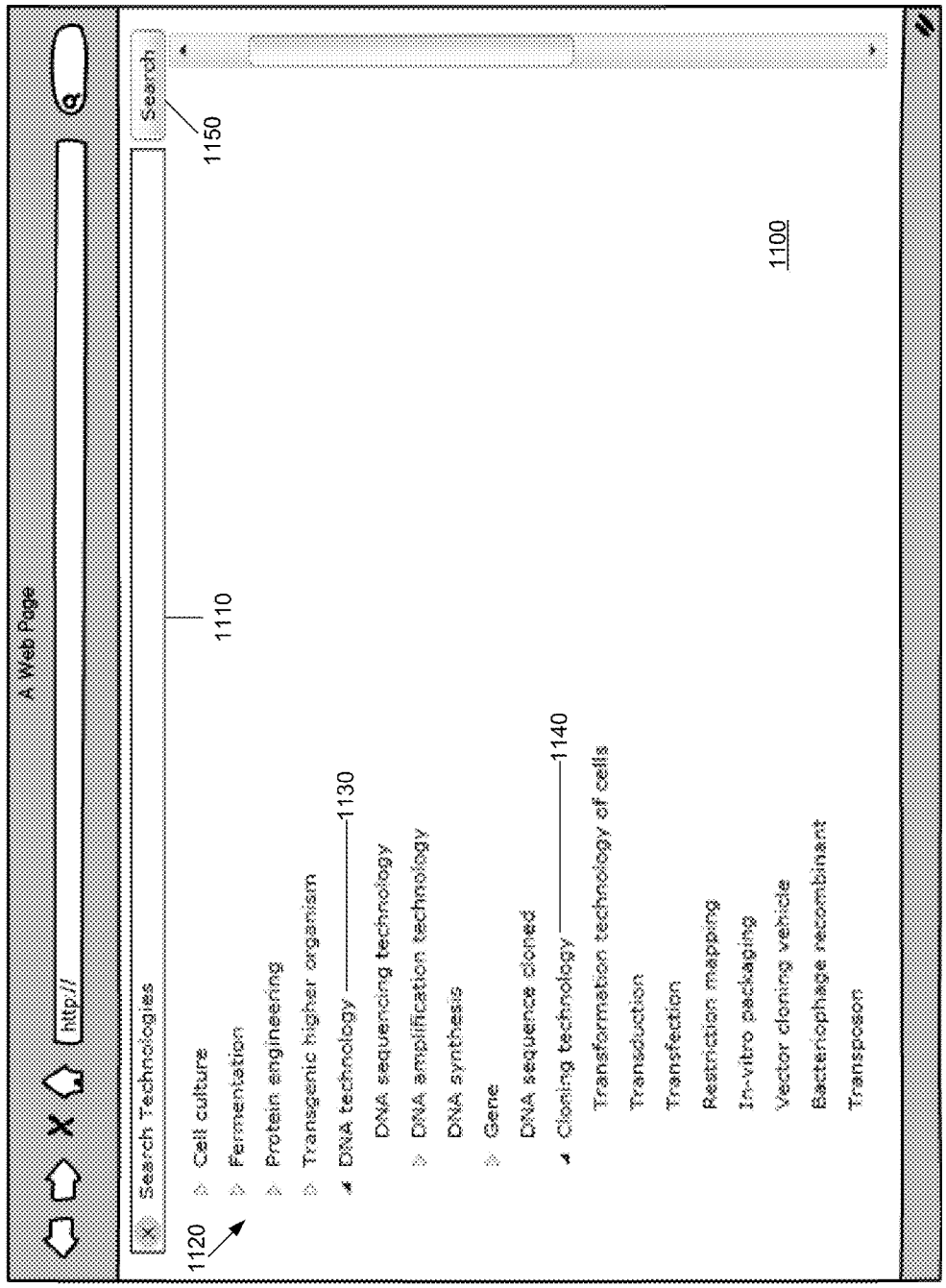
FIG. 11 illustrates an exemplary search interface used to obtain data using the present invention.
Figure 12:
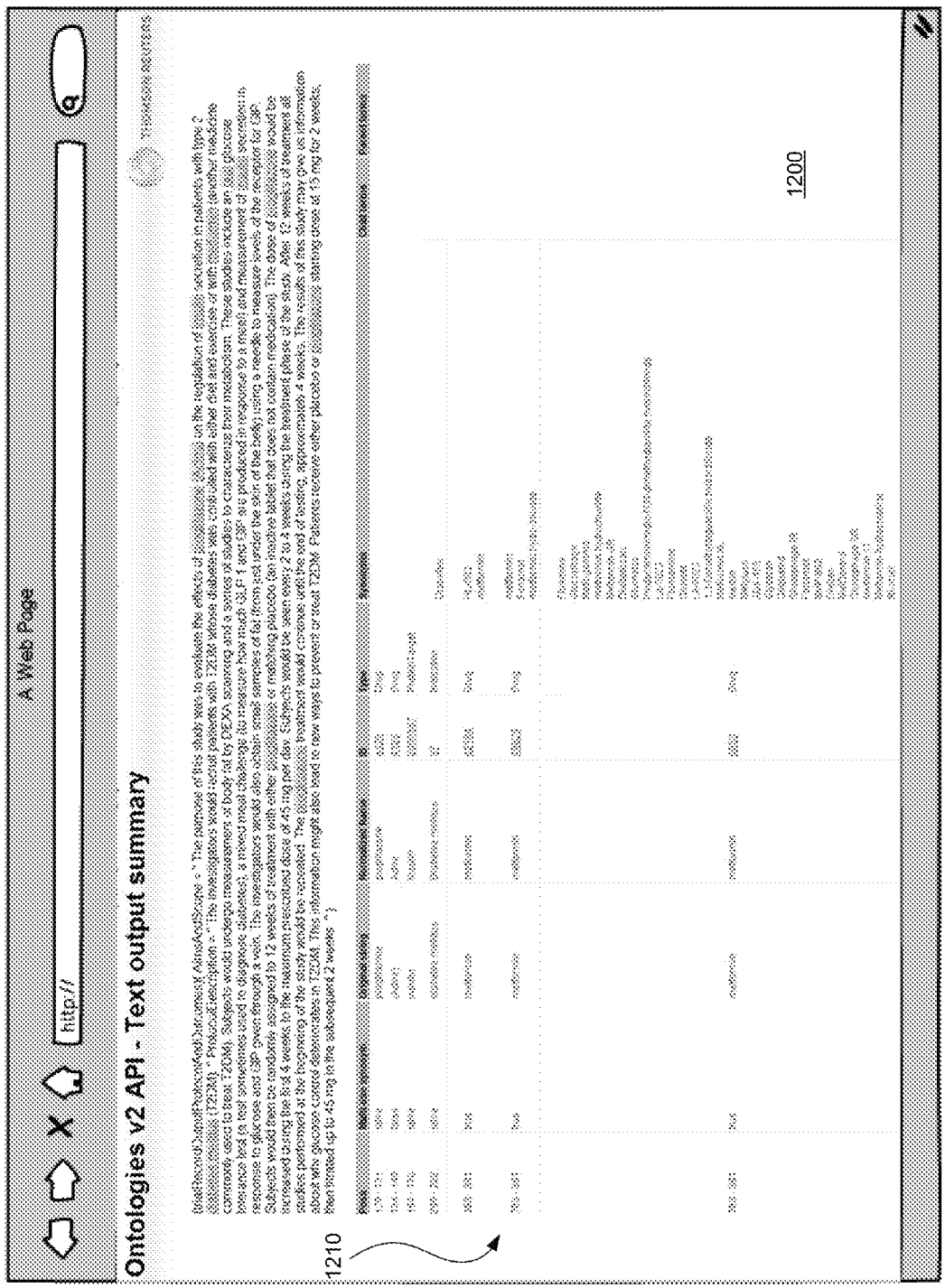
FIG. 12 illustrates an exemplary user interface depicting search results.

With reference now to FIG. 11, a search interface 1100 is provided that allows a user to specify a specific area of focus in which to perform a search. The user has chosen to search technologies from the search field 1110. List 1120 lists all the technologies the user may select from to perform the search. The user may further "drill down" these technologies to specify a detailed area in which to perform a search. By selecting DNA Technology 1130 the user has been presented with a list of technology areas within DNA technology and has further selected Cloning Technology 1140 from the sub-list. Once the user has selected the technology area in which the search is to be performed, the user interacts with the search button 1150 to perform the search. Upon choosing to start the search, the user is presented with text output 1210 found in FIG. 12. Turning now to FIG. 12, an exemplary output screen 1200 is provided that displays the results of the search specified by the user through search interface 1100. The search results 1210 are displayed in tabular form and the user may select from the results to obtain further information, e.g., via active links, etc.

Figure 13:
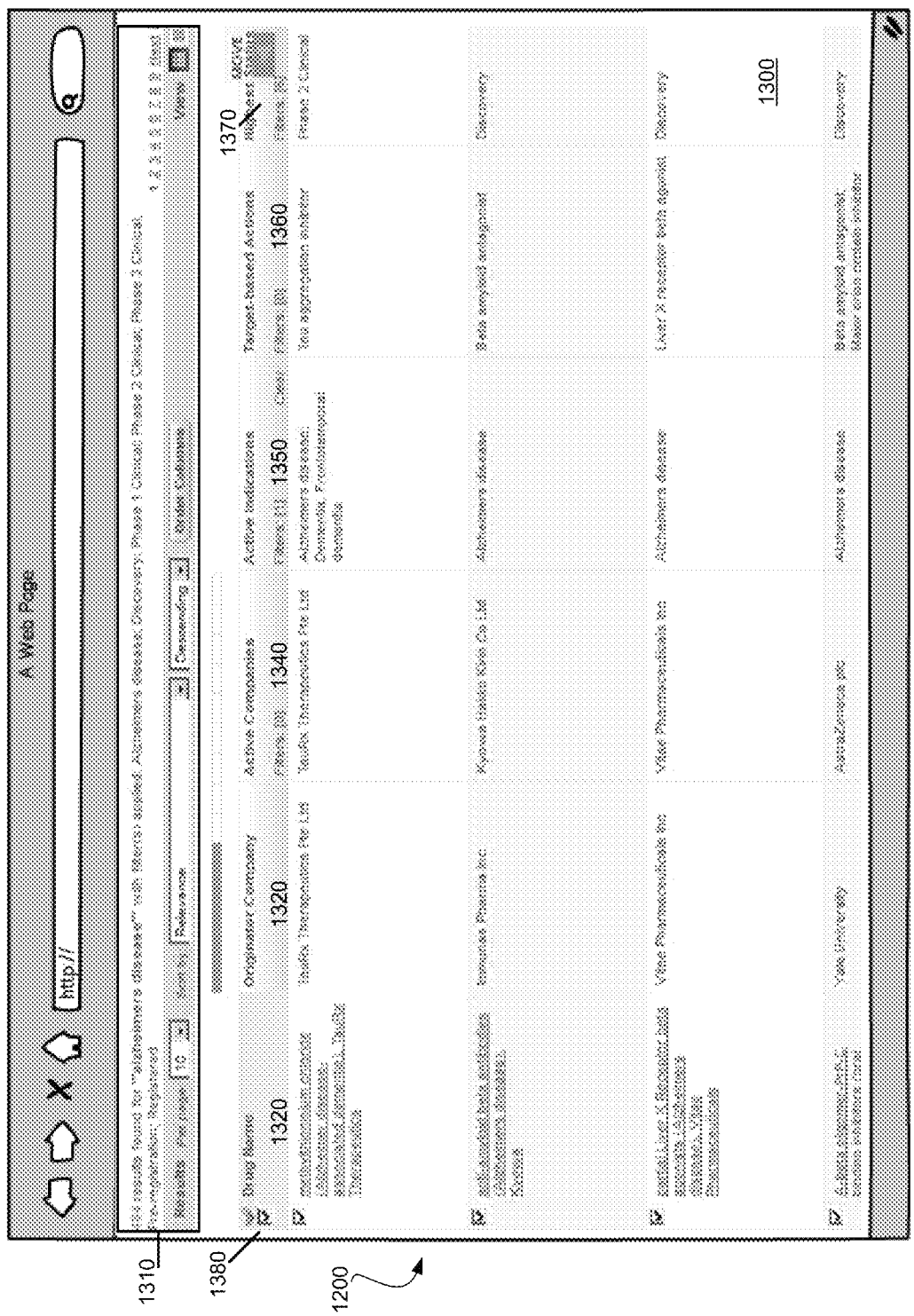
FIG. 13 illustrates an exemplary user interface depicting search results.

With reference now to FIG. 13, a detailed search results screen 1300 is provided showing additional information as it is associated with specific drugs returned as the result of a user search. The user could get to a result like this by either doing a search, from a screen exemplified in FIG. 12, or by clicking on one of the targets in FIGS. 7-10 and expanding to see a list of drugs for that target. The user selected factors associated with the search results is displayed above the results filtering toolbar 1310. The results filtering toolbar can be used to browse the search results 1322 and to further filter the results of the initial search. Columns 1330 through 1370 display specific information about each drug listed in drug name column 1320. The user may select the check boxes in column 1380 to select drugs to be shown in a visual representation of the search results.

The user can navigate to the search screens like that shown in FIG. 12 directly from a home page. The user can navigate to a drug list as shown in FIG. 13, or deal, company, publication, patent lists, from either a search performed on a screen like FIG. 12, or from an entity on one of the visual charts like those shown in FIGS. 7-10.

In implementation, the inventive concepts may be automatically or semi-automatically, i.e., with some degree of human intervention, performed. Also, the present invention is not to be limited in scope by the specific embodiments described herein. It is fully contemplated that other various embodiments of and modifications to the present invention, in addition to those described herein, will become apparent to those of ordinary skill in the art from the foregoing description and accompanying drawings. Thus, such other embodiments and modifications are intended to fall within the scope of the following appended claims. Further, although the present invention has been described herein in the context of particular embodiments and implementations and applications and in particular environments, those of ordinary skill in the art will appreciate that its usefulness is not limited thereto and that the present invention can be beneficially applied in any number of ways and environments for any number of purposes. Accordingly, the claims set forth below should be construed in view of the full breadth and spirit of the present invention as disclosed herein.

We claim:
1. A computer-implemented method comprising:
  a. receiving by a graphical user interface ("GUI") element an input representing a user selected medical issue;
  b. indexing and linking, by an indexing ontologies engine, documents and information in a plurality of databases to generate a set of enriched information to facilitate searching for data relevant to the medical issue;
  c. identifying by use of a processor executing a first identification module comprising a set of code a factor associated with a medical issue;
  d. controlling, by an enterprise server bus, access to a set of assets associated with the medical issue;
  e. identifying by the processor executing a second identification module the set of assets associated with the medical issue based upon the set of enriched information and a set of customizable factors, the set of customizable factors being associated with a user-selected set of weighting factors and comprising a set of scientific factors and a set of business factors, the set of customizable factors including one or more from the group consisting of: drug pipeline data; data on drugs in development; a set of financial metrics associated with a set of companies associated with the medical issue; a set of investment data related to the set of companies; and the relevance of various biological targets and the drugs in development against them to the area of focus;

f. determining for presentation via the GUI a first graphical expression of the relative degree of relatedness of the set of assets associated with the medical issue;

g. receiving a further input representing a user modification of at least one of the set of customizable factors;

h. transforming the first graphical expression of the relative degree of relatedness of the set of assets associated with the medical issue into a second graphical expression of the relative degree of relatedness of the set of assets associated with the medical issue based on the user modification; and i. generating by a representation module for presentation via a display a manipulatable representation of the set of assets.

2. The method of claim 1 wherein the set of assets is further used to identify a second set of assets.

3. The method of claim 2 wherein the set of assets and the second set of assets each is comprised of at least one from the group consisting of: existing drug pipeline data, drug data identified as similar or related to the medical issue, existing financial information, existing disease and disease target research, news, company websites, blogs, conferencing databases, papers, patents, institutions conducting research on the assets or areas of specialization surrounding them, people identified as experts concerning an asset, results and presentations from scientific conferences, registration documents filed with the FDA, papers in peer reviewed journals, and clinical trials registries.

4. The method of claim 3 wherein the manipulatable representation comprises a comparison of an asset from the set of assets with another asset from the second set of assets.

5. The method of claim 1 wherein the factor comprises at least one of a disease, a condition, a gene, and a protein.

6. The method of claim 1 wherein the manipulatable representation is a visual representation.

7. The method of claim 6 wherein the visual representation is selected from among a target grid population, a target graph, a target map, and a target list.

8. The method of claim 6 wherein the visual representation is manipulatable by at least one of a company attribute and a drug attribute.

9. The method of claim 8 wherein the company attribute is at least one of a company type, a funding type, a deal type, and a company history, and wherein the drug attribute is at least one of an indication, an action, a development status, a technology, an indication of whether the user's company has previously assessed the drug, and an existing partnership.

10. The method of claim 1 wherein the set of multiple business factors comprises at least one of partnership status, organization type, publication maturity, target similarity, licensing activity, mergers and acquisitions activity, financial metrics, sales forecasts, private equity funding, existing contracts, types of funding, and prior or current assessment by the user's company.

11. The method of claim 1 wherein the set of multiple scientific factors comprises at least one of drug, drug molecule type, drug development status, related patents, drug licensing deals, drug licensing partnerships, clinical trials, FDA decisions, other regulatory body decisions, disease targets, and drug pathways.

12. The method of claim 1 wherein the set of assets comprises at least one of a company, a partnership, and a set of rights.

13. The method of claim 10 wherein the set of rights comprises at least one of a license, assignment, contract, and sale.

14. The method of claim 1 wherein the medical issue is from the group consisting of: drug, disease, therapy, treatment, medical device, biological target and area of focus in biopharmaceutical research and development.

15. A computer-based system comprising:

a. a server comprising a processor adapted to execute code and a memory for storing executable code;

b. a graphical user interface ("GUI") module comprising a GUI element configured to receive an input representing a user selected medical issue;

c. an indexing ontologies engine configured to index and link documents and information in a plurality of databases to generate a set of enriched information to facilitate searching for data relevant to the medical issue;

d. an enterprise server bus adapted to control access to a set of assets associated with the selected medical issue;

e. a first identification module configured to identify a factor associated with the medical issue;

f. a second identification module configured to identify the set of assets associated with the medical issue based upon the set of enriched information and a set of customizable factors, the set of customizable factors being associated with a user selected set of weighting factors and comprising a set of multiple scientific factors and a set of multiple business factors, the set of customizable factors including one or more from the group consisting of: drug pipeline data; data on drugs in development; a set of financial metrics associated with a set of companies associated with the medical issue; a set of investment data related to the set of companies; and the relevance of various biological targets and the drugs in development against them to the area of focus;

g. a representation module configured to determine for presentation via the GUI module a first graphical expression of the relative degree of relatedness of the set of assets associated with the medical issue;

h. the GUI module further configured to receive a further input representing a user modification of at least one of the set of customizable factors; and i. the representation module further configured to transform the first graphical expression of the relative degree of relatedness of the set of assets associated with the medical issue into a second graphical expression of the relative degree of relatedness of the set of assets associated with the medical issue based on the user modification, and to generate for presentation by a display associated with a user access device a manipulatable representation of the set of assets.

16. The system of claim 15 wherein the set of assets is further used to identify a second set of assets.

17. The system of claim 16 wherein the set of assets and the second set of assets each is comprised of at least one from the group consisting of: existing drug pipeline data, drug data identified as similar or related to the medical issue, existing financial information, existing disease and disease target research, news, company websites, blogs, conferencing databases, papers, patents, institutions conducting research on the assets or areas of specialization surrounding them, people identified as experts concerning an asset, results and presentations from scientific conferences, registration documents filed with the FDA, papers in peer reviewed journals, and clinical trials registries.

18. The system of claim 17 wherein the manipulatable representation comprises a comparison of an asset from the set of assets with another asset from the second set of assets.

19. The system of claim 15 wherein the factor comprises at least one of a disease, a condition, a gene, and a protein.

20. The system of claim 15 wherein the manipulatable representation is a visual representation.

21. The system of claim 20 wherein the visual representation is selected from among a target grid population, a target graph, a target map, and a target list.

22. The system of claim 20 wherein the visual representation is manipulatable by at least one of a company attribute and a drug attribute.

23. The system of claim 22 wherein the company attribute is at least one of a company type, a funding type, a deal type, and a company history, and wherein the drug attribute is at least one of an indication, an action, a development status, a technology, an indication of whether the user's company has previously assessed the drug, and an existing partnership.

24. The system of claim 15 wherein the set of multiple business factors comprises at least one of partnership status, organization type, publication maturity, target similarity, licensing activity, mergers and acquisitions activity, financial metrics, sales forecasts, private equity funding, existing contracts, types of funding, and prior or current assessment by the user's company.

25. The system of claim 15 wherein the set of multiple scientific factors comprises at least one of drug, drug molecule type, drug development status, related patents, drug licensing deals, drug licensing partnerships, clinical trials, FDA decisions, other regulatory body decisions, disease targets, and drug pathways.

26. The system of claim 15 wherein the set of assets comprises at least one of a company, a partnership, and a set of rights.

27. The system of claim 26 wherein the set of rights comprises at least one of a license, assignment, contract, and sale.

28. The system of claim 15 wherein the medical issue is from the group consisting of drug, disease, therapy, treatment, medical device, biological target and area of focus in biopharmaceutical research and development.

* * * * *